(12) United States Patent
Zheng et al.

(10) Patent No.: US 11,952,401 B2
(45) Date of Patent: Apr. 9, 2024

(54) RECOMBINANT FOOT-AND-MOUTH DISEASE VIRUS WITH REDUCED IMMUNOSUPPRESSION ACTIVITY, AND PREPARATION METHOD AND USE THEREOF

(71) Applicant: Lanzhou Veterinary Research Institute, Chinese Academy of Agricultural Sciences, Lanzhou (CN)

(72) Inventors: Haixue Zheng, Lanzhou (CN); Fan Yang, Lanzhou (CN); Zixiang Zhu, Lanzhou (CN); Xiangle Zhang, Lanzhou (CN); Weijun Cao, Lanzhou (CN); Congcong Wang, Lanzhou (CN); Kangli Li, Lanzhou (CN); Huisheng Liu, Lanzhou (CN); Hong Tian, Lanzhou (CN); Keshan Zhang, Lanzhou (CN); Xiangtao Liu, Lanzhou (CN)

(73) Assignee: Lanzhou Veterinary Research Institute, Chinese Academy of Agricultural Sciences, Lanzhou (CN)

(*) Notice: Subject to any disclaimer, the term of this patent is extended or adjusted under 35 U.S.C. 154(b) by 216 days.

(21) Appl. No.: 17/375,203

(22) Filed: Jul. 14, 2021

(65) Prior Publication Data

US 2022/0017576 A1     Jan. 20, 2022

(30) Foreign Application Priority Data

Jul. 14, 2020   (CN) .......................... 202010676834.X

(51) Int. Cl.

| | |
|---|---|
| *C07K 14/005* | (2006.01) |
| *A61K 39/00* | (2006.01) |
| *A61K 39/135* | (2006.01) |
| *A61P 31/14* | (2006.01) |
| *A61P 37/06* | (2006.01) |
| *C12N 7/00* | (2006.01) |

(52) U.S. Cl.
CPC .......... *C07K 14/005* (2013.01); *A61K 39/135* (2013.01); *A61P 31/14* (2018.01); *A61P 37/06* (2018.01); *C12N 7/00* (2013.01); *A61K 2039/525* (2013.01); *A61K 2039/552* (2013.01); *C12N 2770/32121* (2013.01); *C12N 2770/32122* (2013.01); *C12N 2770/32134* (2013.01); *C12N 2770/32152* (2013.01); *C12N 2770/32171* (2013.01)

(58) Field of Classification Search
CPC ................ C07K 14/005; A61K 39/135; A61K 2039/552; A61P 31/14; C12N 2770/32121; C12N 2770/32134
See application file for complete search history.

(56) References Cited

PUBLICATIONS

Zhang et al. Foot-and-Mouth Disease Virus 3B Protein Interacts with Pattern Recognition Receptor RIG-I to Block RIG-I-Mediated Immune Signaling and Inhibit Host Antiviral Response. The Journal of Immunology, 2020, 205: 2207-2221. (Year: 2020).*

* cited by examiner

*Primary Examiner* — Nicole Kinsey White
*Assistant Examiner* — Ruixue Wang
(74) *Attorney, Agent, or Firm* — McDonnell Boehnen Hulbert & Berghoff LLP

(57) ABSTRACT

The present disclosure belongs to the technical field of biological products for veterinary medicine, and specifically relates to a recombinant foot-and-mouth disease virus (FMDV) with a reduced immunosuppressive activity, a preparation method and use thereof, and a recombinant vaccine strain. According to the present disclosure, it is firstly discovered that FMDV 3B protein has an immunosuppressive function, and key sites for exerting the immunosuppressive function are found. A recombinant FMDV vaccine strain with a lost immunosuppressive function in FMDV 3B protein is constructed by introducing amino acid mutations into three repeated copies of FMDV 3B protein.

13 Claims, 6 Drawing Sheets

Specification includes a Sequence Listing.

FIG. 9

SEQUENCE LISTING

<160> NUMBER OF SEQ ID NOS: 26

<210> SEQ ID NO 1
<211> LENGTH: 213
<212> TYPE: DNA
<213> ORGANISM: Artificial Sequence
<220> FEATURE:
<223> OTHER INFORMATION: nucleotide sequence of 3B protein gene coding sequence

<400> SEQUENCE: 1

```
ggaccctacg ccggaccact cgagcgccag agacctctga aagtgagaga gaagctgcca    60
cagcaggagg gaccttacgc cggtccgatg gagagacaga aaccactgaa agtgaaagag    120
aaagccccgg tcgtgaagga aggaccttac gagggaccgg tgaagaagcc tgtcgctttg    180
aaagtgaaag agaagaactt gatcgtcact gag                                  213
```

<210> SEQ ID NO 2
<211> LENGTH: 71
<212> TYPE: PRT
<213> ORGANISM: Artificial Sequence
<220> FEATURE:
<223> OTHER INFORMATION: Amino acid sequence of 3B protein gene coding sequence

<400> SEQUENCE: 2

```
Gly Pro Tyr Ala Gly Pro Leu Glu Arg Gln Arg Pro Leu Lys Val Arg
1               5                   10                  15

Glu Lys Leu Pro Gln Gln Glu Gly Pro Tyr Ala Gly Pro Met Glu Arg
            20                  25                  30

Gln Lys Pro Leu Lys Val Lys Glu Lys Ala Pro Val Val Lys Glu Gly
        35                  40                  45

Pro Tyr Glu Gly Pro Val Lys Lys Pro Val Ala Leu Lys Val Lys Glu
    50                  55                  60

Lys Asn Leu Ile Val Thr Glu
65                  70
```

<210> SEQ ID NO 3
<211> LENGTH: 213
<212> TYPE: DNA
<213> ORGANISM: Artificial Sequence
<220> FEATURE:
<223> OTHER INFORMATION: nucleotide sequence of 3B protein of a wild-type FMDV O/BY/CHA/2010 strain

<400> SEQUENCE: 3

```
ggaccctacg ccggaccact cgagcgccag agacctctga aagtgagagc caagctgcca    60
cagcaggagg gaccttacgc cggtccgatg gagagacaga aaccactgaa agtgaaagcg    120
aaagccccgg tcgtgaagga aggaccttac gagggaccgg tgaagaagcc tgtcgctttg    180
aaagtgaaag ctaagaactt gatcgtcact gag                                  213
```

<210> SEQ ID NO 4
<211> LENGTH: 71
<212> TYPE: PRT
<213> ORGANISM: Artificial Sequence
<220> FEATURE:
<223> OTHER INFORMATION: amino acid sequence of 3B protein of a wild-type FMDV O/BY/CHA/2010 strain

<400> SEQUENCE: 4

```
Gly Pro Tyr Ala Gly Pro Leu Glu Arg Gln Arg Pro Leu Lys Val Arg
1               5                   10                  15

Ala Lys Leu Pro Gln Gln Glu Gly Pro Tyr Ala Gly Pro Met Glu Arg
            20                  25                  30

Gln Lys Pro Leu Lys Val Lys Ala Lys Ala Pro Val Val Lys Glu Gly
        35                  40                  45

Pro Tyr Glu Gly Pro Val Lys Lys Pro Val Ala Leu Lys Val Lys Ala
    50                  55                  60

Lys Asn Leu Ile Val Thr Glu
65                  70
```

<210> SEQ ID NO 5
<211> LENGTH: 3591
<212> TYPE: DNA
<213> ORGANISM: Artificial Sequence
<220> FEATURE:
<223> OTHER INFORMATION: gene fragments of the O/JSCZ/2013 virus strain

<400> SEQUENCE: 5

```
cttaagggac aggaacacgc cgtgtttgcc tgcgtcacct ccaacgggtg gtacgcgatc      60
gacgacgaag aattctaccc ctggacgcca gatccgtccg acgtgctggt ctttgtcccg     120
tacgatcaag aaccacttaa tggagaatgg aaagcaaggg ttcagagacg gctcaaggga     180
gccggacaat ccagtccggc tactgggtca cagaaccaat caggcaacac cgggagtatc     240
atcaacaatt actacatgca gcaataccag aactccatgg acacccaact tggtgacaat     300
gctatcagcg gaggctccaa cgagggatcc acagacacaa cctccaccca cacaaccaac     360
actcagaaca atgactggtt ttcaaagttg gccagctctg ccttcagcgg tcttttcggc     420
gccctcctcg ccgataagaa aaccgaggag accactcttc tcgaggaccg catcctcacc     480
acccgaaacg gacacaccac ctcgacaacc cagtcgagtg ttggcataac gcacgggtac     540
gcaacagctg aggattttgt gaacgggcca acacctctg tcttgagac cagagttgtc      600 caggcggaac ggttctttaa aacccacctg ttcgactggg tcaccagtga tccgttcgga     660
cggtactact tgttggagct cccgactgac acaaaggtg tctacggcag cctgaccgac     720
tcatacgcct acatgagaaa cggttgggat gttgaggtca ccgctgtggg gaatcagttc     780 aacgaggct gcctactggt ggccatggta cctgaacttt gttccatcga gcggagagag     840
ctgttccagc ttacgctctt ccccaccag ttcatcaacc cccggacgaa catgacagcc     900
cacatcaagg tgccctttgt tggcgtcaac cgttacgatc agtacaaggt acacaagccg     960 tggaccccttg tggttatggt cgtagcccca ctgactgtca caccgaagg cgctccgcag    1020 atcaaggtgt atgccaacat cgcacccacc aacgtgcacg tcgcgggtga gttcccttcc    1080
aaagagggga ttttccctgt ggcctgtagc gacggttatg gcggcttggt gacaactgac    1140
ccaaagacgc tgacccccgt ttacggcaaa gtgttcaacc ccccgcaa catgttgccg    1200 gggcggttca ccaacctcct gggcgtggct gaggcttgcc ccacgtttct gcacttcgat    1260
ggtgacgtac cgtatgtgac cactaagacg gattcggaca gggtgctcgc acaatttgac    1320 ttgtcttgg cagcaaaaca catgtcaaac accttccttg caggtcttgc ccagtactac    1380
acgcagtaca gcggcaccgt taacctgcac ttcatgttca caggtcccac tgacgcgaaa    1440
gcgcgttaca tgattgcgta tgcccctccg ggcatggagc cgcccaaaac acctgaggct    1500
gctgctcact gcattcacgc agagtgggac acgggtctga actcaaagtt tacctttttcc    1560 atccctacc tctcggcggc tgattacgcg tacaccgcgt ctgacgctgc tgagaccaca    1620
aatgttcagg gatgggtctg cttattcaa ataacacacg gaaagctga gggtgacgct    1680 cttgtcgtgc tggccagtgc tggcaaagac tttgagctgc gcctgccttgt ggacgctcgg    1740 caacagacca cttcgacggg cgagtcggct gaccccgtga ctgccaccgt tgagaattac    1800
ggtggcgaga cacaggtcca gaggcgccac cacacagacg tctcattcat attggacaga    1860
tttgtgaaag tcacaccaaa agactcaata aatgtattgg acctgatgca daccccctcc    1920 cacacccctag taggggcgct cctccgcact gccacttact atttcgctga tctagaggtg    1980
gcagtgaaac acaagggga ccttacctgg gtgccaaatg gagcacctga agcagccttg    2040
gacaacacca ccaacccaac ggcgtactat aaggcgccgc ttaccccggct tgcattgccc    2100
```

```
tacacggcac cacaccgtgt tttggccacc gtttacaacg ggaaatgcaa atacgccggg    2160
ggctcactgc ccaacgtgag aggcgatctc caagagctgg ctcagaaggc agcgaggccg    2220
ctgcctactt ctttcaacta cggtgccatc aaagccactc gggtgacaga actgctgtac    2280
cgcatgaaga gggccgagac gtactgtcct cggccccttt tggctgttca cccgagtgcg    2340
gccagacaca aacagaaaat agtggcgcct gtaaagcagt ccttgaactt tgatctgctc    2400
aagttggcag gggacgtgga gtccaaccct gggcccttct tcttctctga cgtcaggtca    2460
aacttcacca aactggtgga aaccatcaac cagatgcaag aggacatgtc aacaaaacac    2520
ggacccgact ttaaccggtt ggtatcagcg tttgaggaat tggccgctgg ggtgaaagcc    2580
atcaggaccg gcctcgacga ggccaaaccc tggtacaagc tcatcaagct cctgagccgc    2640
ttgtcatgca tggccgctgt agcagcacgg tccaaggacc cagtccttgt ggctatcatg    2700
ctggctgaca ccggtcttga gattctggac agcacatttg tcgtgcagaa aatctccgac    2760
tccctctcca gtctctttca cgtgccggcc cccgtcttca gtttcggagc tccgattctg    2820
ctagccgggt tggtcaaggt cgcctcgagc ttcttccggt ccacacccga ggatctcgag    2880
agagcagaga aacagctcaa agcacgtgac atcaatgaca tcttcgccat tctcaagaac    2940
ggcgagtggc tggtcaagtt gatcctagcc atccgcgact ggattaaagc atggatcgcc    3000
tcagaagaga agtttgtcac catgacagac ttggtgcctg catccttga aaagcagcgg     3060 gacctcaacg acccggccaa gtacaaggaa gccaaggaat ggctcgacaa cgcgcgccaa    3120
acgtgtttga agagcgggaa cgtccacatt gccaacctgt gcaaagtggt cgccccagca    3180
ccgagcaagt cgagacctga accgtggtc gtgtgcctcc gcggcaaatc cggtcagggt     3240
aagagtttcc ttgcgaacgt gctggcacaa gccatctcta cccactttac cggcaggact    3300
gactcagttt ggtactgtcc gccagaccct gaccacttcg acggttacaa ccagcagacc    3360
gttgttgtga tggatgattt gggccagaat cccgacggca aggacttcaa gtacttcgcc    3420
cagatggtct cgaccacggg gttcatcccg cccatggctt cacttgagga caaaggcaag    3480
cctttcaaca gcaaagtcat cattgccacc accaacctgt actcgggctt caccccgaga    3540
accatggtgt gccccgatgc gctgaaccga aggtttcact tgacatcga t              3591
```

<210> SEQ ID NO 6
<211> LENGTH: 71
<212> TYPE: PRT
<213> ORGANISM: Artificial Sequence
<220> FEATURE:
<223> OTHER INFORMATION: amino acid encoded by the mutated 3B gene

<400> SEQUENCE: 6

Gly Pro Tyr Thr Gly Pro Leu Glu Arg Gln Lys Pro Leu Lys Val Arg
1               5                   10                  15

Glu Lys Leu Pro Gln Gln Glu Gly Pro Tyr Ala Gly Pro Met Glu Arg
            20                  25                  30

Gln Lys Pro Leu Lys Val Lys Glu Lys Ala Pro Val Val Lys Glu Gly
        35                  40                  45

Pro Tyr Glu Gly Pro Val Lys Lys Pro Val Ala Leu Lys Val Lys Glu
    50                  55                  60

Lys Asn Leu Ile Val Thr Glu
65                  70

<210> SEQ ID NO 7
<211> LENGTH: 71

<212> TYPE: PRT
<213> ORGANISM: Artificial Sequence
<220> FEATURE:
<223> OTHER INFORMATION: amino acid sequence of parental FMDV 3B protein

<400> SEQUENCE: 7

Gly Pro Tyr Thr Gly Pro Leu Glu Arg Gln Lys Pro Leu Lys Val Arg
1               5                   10                  15

Ala Lys Leu Pro Gln Gln Glu Gly Pro Tyr Ala Gly Pro Met Glu Arg
            20                  25                  30

Gln Lys Pro Leu Lys Val Lys Val Lys Ala Pro Val Val Lys Glu Gly
        35                  40                  45

Pro Tyr Glu Gly Pro Val Lys Lys Pro Val Ala Leu Lys Val Lys Ala
    50                  55                  60

Lys Asn Leu Ile Val Thr Glu
65                  70

<210> SEQ ID NO 8
<211> LENGTH: 2373
<212> TYPE: DNA
<213> ORGANISM: Artificial Sequence
<220> FEATURE:
<223> OTHER INFORMATION: gene fragments of the A/WH/CHA/09 virus strain

<400> SEQUENCE: 8
cttaagggac aggaacacgc agtgtttgcc tgtgttacct ccaacgggtg gtacgcgatt      60
gacgacgagg acttttaccc ctggacacca gacccgtctg atgtcctggt gtttgtcccg     120
tatgatcaag aaccactcaa cggagaatgg aaaacaaagg ttcagaggcg acttaaaggg     180
gcagggcaat ctagccccgc accgggtcg cagaaccagt caggcaatac cggcagcatc      240
attaacaact actacatgca gcagtaccag aactccatgg acacacaact tggtgacaac     300
gccatcagcg gaggatccaa cgaggggtcc acggacacaa cctctaccca cacaaccaac     360
acccaaaaca atgactggtt ctcaaaactg caagttctg cattcaccgg tcttttcggc      420
gcactgctcg ccgacaagaa gaccgaagag acaactcttc tggaggaccg tatcctcacc     480
actcgtaatg acacaccac tctacaact cagtcgagtg tgggggtcac ctacgggtat       540
tcaactggtg aggaccacgt ttctggacct aacacatcag gtttggagac gcgggtggta     600
caagctgaaa ggttcttcaa gaagcacttg tttgattgga caacggacaa acccttggt      660 cacattgaaa agctggaact tcccactgat cacaaaggtg tctacggaca gctggtggac     720
tcctttgcat acatgagaaa tggctggac gtggaggtgt ctgctgttgg caaccagttc      780
aacggcgggt gccttctcgt ggccatggta cctgagttta aggagttcac cacacgtgaa     840
aagtaccagc tcaccctgtt ccccaccag ttcattagcc ccagaaccaa catgaccgcg      900
cacatcacgg tcccgtacct tggtgtgaac aggtatgacc agtacaacaa acacaaaccc     960
tggacgttgg tggtgatggt ggtttcgcca cttaccacta gctccattgg tgcatcacag    1020
attaaggtct acaccaacat cgccccgacc acgttcacg tggctggcga gctcccgtcg      1080
aaagagggga tcgtgccagt cgcctgctcg gacgggtacg gtggcctggt gacaacagac    1140
cctaaaacag ctgaccctgc ttacggtatg gtgtacaacc cacctaggac caactacccc    1200
gggcggttta caaacttgtt ggacgtggca gaggcgtgcc ccaccttcct ctgtttcgac    1260
gacgggaaac cgtacgttgt gacaagaacg gacgagcagc gcctcttggc caagtttgac    1320
ctttcccttg ctgcaaagca catgtcaaac acctaccttt cagggatagc acagtactac    1380
gcacagtact ctggcaccat caatttgcac ttcatgttta ctggttccac tgactcaaag    1440

```
gcccgttaca tggtggctta cgtcccgccc ggcgtgacaa cgccaccgga cacgcctgag    1500
agagctgcgc actgcatcca cgcagaatgg gacacggggc taaactccaa attcactttt    1560
tcaatcccat acgtatctgc tgcagattac gcgtacacag cgtccgatgt ggcagacaca    1620
acaaacgtac agggatgggt ttgcatctac caaatcaccc atgggaaggc cgaacaagac    1680
actctggttg tgtcggtcag cgccggcaaa gactttgagc tgcgcctccc cattgacccc    1740
cgtgcgcaaa ccaccgccac cggggaatca gcagaccccg tcacaaccac cgtcgagaac    1800
tacggtggtg agacacaagt gcagcgacgc caccacaccg acgtcagctt cataatggac    1860
aggtttgtgc aaatcaagcc tgtgagcccc acacatgtca ttgacctcat gcaaacacac    1920
caacacgggc tggtgggcgc tatgttgcgc gcggccacct actactttc tgatcttgag     1980 attgtggtga accacacggg tcgcctaacg tgggtaccca atggagcacc tgaggcagca    2040
ctggacaaca cgagcaaccc cactgcttac cacaaagcac cgttcacacg gcttgcactc    2100
ccttacaccg cgccacaccg cgtgttggca actgtgtaca acgggaatag caagtactct    2160
gcgcctgcaa cacggcgagg tgacttgggg tctctcgcgg cgaggctcgc cgcacagctt    2220
cctgcctcct tcaactacgg cgcgattcga gccacggaga tccaagaact cctcgtgcgc    2280
atgaagcgtg ccgagctcta ctgccccagg ccactgctgg cggtggaggt gacgtcacaa    2340
gacagacaca agcagaaaat tattgcaccg gtg                                 2373

<210> SEQ ID NO 9
<211> LENGTH: 38
<212> TYPE: DNA
<213> ORGANISM: Artificial Sequence
<220> FEATURE:
<223> OTHER INFORMATION: forward primer of 3B-HindIII restriction enzyme

<400> SEQUENCE: 9
ctcaagcttg ccaccatggg accctacgcc ggaccact                             38

<210> SEQ ID NO 10
<211> LENGTH: 31
<212> TYPE: DNA
<213> ORGANISM: Artificial Sequence
<220> FEATURE:
<223> OTHER INFORMATION: reverse primer of  BamHI restriction enzyme

<400> SEQUENCE: 10
atggatcctc actcagtgac gatcaagttc t                                   31

<210> SEQ ID NO 11
<211> LENGTH: 55
<212> TYPE: DNA
<213> ORGANISM: Artificial Sequence
<220> FEATURE:
<223> OTHER INFORMATION: oligNot I primer

<400> SEQUENCE: 11
ttttctagag cggccgcttt tttttttttt tttttttttt tttttttttt ttttt         55

<210> SEQ ID NO 12
<211> LENGTH: 40
<212> TYPE: DNA
<213> ORGANISM: Artificial Sequence
<220> FEATURE:
<223> OTHER INFORMATION: Amplification primer forward sequence of OP12A

<400> SEQUENCE: 12
```

```
ttttccttaa gggacaggaa cacgccgtgt ttgcctgcgt                    40
```

<210> SEQ ID NO 13
<211> LENGTH: 29
<212> TYPE: DNA
<213> ORGANISM: Artificial Sequence
<220> FEATURE:
<223> OTHER INFORMATION: Amplification primer reverse sequence of OP12A

<400> SEQUENCE: 13

```
actcacatcg atgtcaaagt gaaaccttc                               29
```

<210> SEQ ID NO 14
<211> LENGTH: 37
<212> TYPE: DNA
<213> ORGANISM: Artificial Sequence
<220> FEATURE:
<223> OTHER INFORMATION: Mutation primer forward sequence of protein 3B1

<400> SEQUENCE: 14

```
aaaacctctg aaagtgagag agaagctccc acagcag                      37
```

<210> SEQ ID NO 15
<211> LENGTH: 37
<212> TYPE: DNA
<213> ORGANISM: Artificial Sequence
<220> FEATURE:
<223> OTHER INFORMATION: Mutation primer reverse sequence of protein 3B1

<400> SEQUENCE: 15

```
ctgctgtggg agcttctctc tcactttcag aggtttt                      37
```

<210> SEQ ID NO 16
<211> LENGTH: 37
<212> TYPE: DNA
<213> ORGANISM: Artificial Sequence
<220> FEATURE:
<223> OTHER INFORMATION: Mutation primer forward sequence of protein 3B2

<400> SEQUENCE: 16

```
gaaaccgctg aaagtgaaag agaaagcccc ggtcgtt                      37
```

<210> SEQ ID NO 17
<211> LENGTH: 37
<212> TYPE: DNA
<213> ORGANISM: Artificial Sequence
<220> FEATURE:
<223> OTHER INFORMATION: Mutation primer reverse sequence of protein 3B2

<400> SEQUENCE: 17

```
aacgaccggg gctttctctt tcactttcag cggtttc                      37
```

<210> SEQ ID NO 18
<211> LENGTH: 37
<212> TYPE: DNA
<213> ORGANISM: Artificial Sequence
<220> FEATURE:
<223> OTHER INFORMATION: Mutation primer forward sequence of protein 3B3

<400> SEQUENCE: 18

```
tgtcgctttg aaagtgaaag agaagaactt gattgtc                      37
```

<210> SEQ ID NO 19
<211> LENGTH: 37
<212> TYPE: DNA
<213> ORGANISM: Artificial Sequence

```
<220> FEATURE:
<223> OTHER INFORMATION: Mutation primer reverse sequence of protein 3B3

<400> SEQUENCE: 19
gacaatcaag ttcttctctt tcactttcaa agcgaca                                37

<210> SEQ ID NO 20
<211> LENGTH: 40
<212> TYPE: DNA
<213> ORGANISM: Artificial Sequence
<220> FEATURE:
<223> OTHER INFORMATION: Amplification primer forward sequence of AP1

<400> SEQUENCE: 20
ttttccttaa gggacaggaa catgctgtgt ttgcctgcgt                             40

<210> SEQ ID NO 21
<211> LENGTH: 39
<212> TYPE: DNA
<213> ORGANISM: Artificial Sequence
<220> FEATURE:
<223> OTHER INFORMATION: Amplification primer reverse sequence of AP1

<400> SEQUENCE: 21
tattttcacc ggtgcaataa ttttctgctt gtgtctgtc                              39

<210> SEQ ID NO 22
<211> LENGTH: 71
<212> TYPE: PRT
<213> ORGANISM: Artificial Sequence
<220> FEATURE:
<223> OTHER INFORMATION: amino sequence of FMDV 3B protein

<400> SEQUENCE: 22

Gly Pro Tyr Ala Gly Pro Leu Glu Arg Gln Lys Pro Leu Lys Val Arg
1               5                   10                  15

Ala Lys Leu Pro Gln Gln Glu Gly Pro Tyr Ala Gly Pro Met Glu Arg
            20                  25                  30

Gln Lys Pro Leu Lys Val Lys Ala Lys Ala Pro Val Val Lys Glu Gly
        35                  40                  45

Pro Tyr Glu Gly Pro Val Lys Lys Pro Val Ala Leu Lys Val Lys Ala
    50                  55                  60

Lys Asn Leu Ile Val Thr Glu
65                  70

<210> SEQ ID NO 23
<211> LENGTH: 71
<212> TYPE: PRT
<213> ORGANISM: Artificial Sequence
<220> FEATURE:
<223> OTHER INFORMATION: amino sequence of FMDV Type O GD 3B

<400> SEQUENCE: 23

Gly Pro Tyr Ala Gly Pro Leu Glu Arg Gln Lys Pro Leu Lys Val Arg
1               5                   10                  15

Ala Lys Leu Pro Gln Gln Glu Gly Pro Tyr Ala Gly Pro Met Glu Arg
            20                  25                  30

Gln Lys Pro Leu Lys Val Lys Ala Lys Ala Pro Val Val Lys Glu Gly
        35                  40                  45

Pro Tyr Glu Gly Pro Val Lys Lys Pro Val Ala Leu Lys Val Lys Ala
    50                  55                  60

Lys Asn Leu Ile Val Thr Glu
```

-continued

<210> SEQ ID NO 24
<211> LENGTH: 71
<212> TYPE: PRT
<213> ORGANISM: Artificial Sequence
<220> FEATURE:
<223> OTHER INFORMATION: amino sequence of FMDV Type O CH 3B

<400> SEQUENCE: 24

```
Gly Pro Tyr Thr Gly Pro Leu Glu Arg Gln Lys Pro Leu Lys Val Arg
1               5                   10                  15

Ala Lys Leu Pro Gln Gln Glu Gly Pro Tyr Ala Gly Pro Met Glu Arg
            20                  25                  30

Gln Lys Pro Leu Lys Val Lys Val Lys Ala Pro Val Val Lys Glu Gly
        35                  40                  45

Pro Tyr Glu Gly Pro Val Lys Lys Pro Val Ala Leu Lys Val Lys Ala
    50                  55                  60

Lys Asn Leu Ile Val Thr Glu
65                  70
```

<210> SEQ ID NO 25
<211> LENGTH: 71
<212> TYPE: PRT
<213> ORGANISM: Artificial Sequence
<220> FEATURE:
<223> OTHER INFORMATION: amino sequence of FMDV Type A 3B

<400> SEQUENCE: 25

```
Gly Pro Tyr Ala Gly Pro Leu Glu Arg Gln Lys Pro Leu Lys Val Arg
1               5                   10                  15

Ala Lys Leu Pro Gln Gln Glu Gly Pro Tyr Ala Gly Pro Leu Glu Arg
            20                  25                  30

Gln Lys Pro Leu Lys Val Lys Val Lys Ala Pro Val Val Lys Glu Gly
        35                  40                  45

Pro Tyr Glu Gly Pro Val Lys Lys Pro Val Ala Leu Lys Val Lys Ala
    50                  55                  60

Lys Asn Leu Ile Val Thr Glu
65                  70
```

<210> SEQ ID NO 26
<211> LENGTH: 71
<212> TYPE: PRT
<213> ORGANISM: Artificial Sequence
<220> FEATURE:
<223> OTHER INFORMATION: amino sequence of FMDV Type Asia 1 3B

<400> SEQUENCE: 26

```
Gly Pro Tyr Ala Gly Pro Leu Glu Arg Gln Lys Pro Leu Glu Val Arg
1               5                   10                  15

Ala Lys Leu Pro Gln Gln Glu Gly Pro Tyr Ala Gly Pro Met Glu Arg
            20                  25                  30

Gln Lys Pro Leu Lys Val Lys Ala Lys Ala Pro Val Val Lys Glu Gly
        35                  40                  45

Pro Tyr Glu Gly Pro Val Lys Lys Pro Val Ala Leu Lys Val Lys Ala
    50                  55                  60

Lys Asn Leu Ile Val Thr Glu
65                  70
```

RECOMBINANT FOOT-AND-MOUTH DISEASE VIRUS WITH REDUCED IMMUNOSUPPRESSION ACTIVITY, AND PREPARATION METHOD AND USE THEREOF

CROSS REFERENCE TO RELATED APPLICATION(S)

This patent application claims the benefit and priority of Chinese Patent Application No. 202010676834.X filed on Jul. 14, 2020, the disclosure of which is incorporated by reference herein in its entirety as part of the present application.

SEQUENCED LISTING STATEMENT

A computer readable form of the Sequence Listing is filed with this application by electronic submission and is incorporated into this application by reference in its entirety. The Sequence Listing is contained in the file created on Sep. 28, 2021 having the file name "21-0921-US_SeqList.txt" and is 19 kb in size

TECHNICAL FIELD

The present disclosure belongs to the technical field of bioengineering, and specifically relates to a recombinant foot-and-mouth disease virus (FMDV) with reduced immunosuppressive function, a preparation method and use thereof, and a recombinant vaccine strain.

BACKGROUND ART

Foot-and-mouth disease (FMD) is an acute, febrile, and highly contagious viral disease that mainly affects domestic animals and wild cloven-hoofed animals. Generally, FMD is rarely fatal in adult livestock, it causes serious production losses. In addition, severe mortality may occur in young animals. FMD has a relatively-high incidence in natural hosts, and shows typical lesions in different species. In the case of infection in young animals or pandemics in wild animals, the FMD may cause a higher mortality rate. The FMD has been listed as a Class A infectious disease by the World Organization for Animal Health (OIE), and as a Class I animal disease in China.

FMD is caused by the foot-and-mouth disease virus (FMDV), accompanied by blisters around the hoof, mouth, and breasts; and the blisters rupture to form ulcers. FMDV-affected animals will experience lameness, depression, anorexia, excessive salivation, etc. In most cases, coronet and capsula ungula will fall off during the infection. FMDV may also cause damage to the reproductive system of animals, typically to sheep and goats. Most adult animals will recover within 2-3 weeks after infection with FMDV, and have a slightly-longer recovery time from a secondary infection. Complications that may occur after the animal has recovered from infection include temporary or permanent reduction in milk production, hoof deformity, lameness, chronic mastitis, and weight loss, etc.

In recent years, many countries adopt the prevention and control policy focusing on compulsory vaccine immunization, and has achieved relatively-desirable prevention and control effects. However, FMDV may escape from host immune system and exists for a long time, resulting in the difficulty of eradication of FMD. More importantly, FMDV targets host immune pathway molecules through viral proteins to suppress the activation of host immune pathways and suppress the production of interferons, thereby exerting an antagonistic effect. The immunosuppression by the virus antagonizes the host immune response. This is conducive to the survival of immune-escape mutant virus strains, causing persistent infections, and complicating the prevention and control of the FMD. In order to completely eradicate FMD, there is an urgent need of a novel vaccine that may improve the immune efficacy, and eliminate the immunosuppressive ability, and reduce or block the occurrence of persistent infections. To solve this problem, investigation of the mechanism by FMDV to escape host immune response and identification of the relevant viral proteins involved in immunosuppression is critical for development of new anti-virals and novel vaccines.

The FMDV genome consists of a 5' non-coding region, an open reading frame (ORF) and a 3' non-coding region. The ORF encodes a polyprotein, which is gradually cleaved into mature structural and non-structural proteins of the virus. The ORF specifically includes an L-protein coding region, a P1 region, a P2 region and a P3 region; the L-protein coding region has two start codons separated by 84 bases, and encodes Lab, Lb and two non-structural proteins; the P1 region encodes four structural proteins, VP4, VP2, VP3, and VP1, which participate in the assembly of viral capsids; the P2 region encodes three non-structural proteins 2A, 2B, and 2C; and the P3 region encodes four non-structural proteins, 3A, 3B, 3C$^{pro}$, and 3D$^{pro}$. 3B protein is an important virulence factor of FMDV that binds to the N-terminal of the 5' non-coding region of FMDV, functioning as a primer to initiate 3D protein (RNA polymerase) for synthesis of viral RNA. FMDV 3B protein has 3 highly-homologous copies, named 3B1, 3B2 and 3B3. This is also the difference between FMDV and other picornaviruses. In addition, the amino acid sequences of 3B1, 3B2 and 3B3 of different serotypes of FMDV are highly-homologous. A specific sequence comparison result is shown in FIG. 1. Meanwhile, the 3B protein can regulate the function of FMDV 3A protein, affecting virus replication. Therefore, FMDV 3B protein has multiple functions during FMDV replication. Furthermore, an enzyme-linked immunosorbent assay (ELISA) method based on FMDV 3ABC non-structural protein has been widely used in the diagnosis of FMDV infection. Accordingly, it is of important significance and potential application in the related diagnosis and development of prevention and control products around 3B protein. In recent years, reverse genetic manipulation technology has been widely used to modify biological characteristics of viruses, such as virulence or virus yield. At present, there is no report to target FMDV 3B protein using the reverse genetic manipulation technology to modify the biological characteristics of FMDV such as virulence or yield of FMDV.

In view of this, the present disclosure discovers that FMDV 3B protein has an immunosuppressive function, and constructs a series of 3B plasmid mutants through mutation PCR, gene synthesis and other methods, thus determining the key sites for the immunosuppressive function. The present disclosure, by introducing amino acid mutations into the key sites of three repeated copies of the 3B protein, constructs a recombinant FMDV with elimination of 3B protein immunosuppressive activity; where the recombinant FMDV may be stably passaged in an FMDV propagation cell line, the baby hamster kidney cell line 21 (BHK-21), which is defective in the interferon production, and does not affect virus yields. However, the recombinant FMDV has a declined virulence in pig-derived host cells, and exerts a stronger inducing ability of innate immune response, such that the recombinant FMDV may be used as a recombinant vaccine strain. The present disclosure prepares the obtained recombinant vaccine strain into an inactivated vaccine that may promote early immune response, and induce high-level antibody production, thereby improving biological safety and immune effectiveness of the vaccine. The present disclosure has good application prospects.

SUMMARY

In view of the above technical problem, the present disclosure proposes an idea for constructing a recombinant FMDV and for preparing a recombinant FMDV vaccine strain from the recombinant FMDV. The idea is achieved through the following technical solutions:

The present disclosure has discovered that foot-and-mouth disease virus (FMDV) 3B protein has relatively strong immunosuppressive function and can be used to prepare immunosuppressive medicines or reagents. Based on this, the present disclosure provides use of FMDV 3B protein in the preparation of an immunosuppressant.

The present disclosure further provides a preparation method of a recombinant FMDV by losing only an immunosuppressive function of FMDV 3B protein. FMDV 3B protein not only has an immunosuppressive function, but also binds to the N-terminal of the 5' non-coding region to initiate viral 3D protein (RNA polymerase) for synthesis of viral RNA and further regulate the function of FMDV 3A protein, thus affecting the replication of the virus and the like. Therefore, the present disclosure can relieve the ability of FMDV 3B protein to suppress the innate immune response by losing only the immunosuppressive function of FMDV 3B protein without affecting other functions of FMDV 3B protein, thereby reducing the pathogenicity of FMDV to the host. The method of the present disclosure can be used to prepare a recombinant FMDV.

The present disclosure further provides a preparation method of a recombinant FMDV vaccine strain by losing only an immunosuppressive function of FMDV 3B protein. FMDV 3B protein not only has an immunosuppressive function, but also binds to the N-terminal of the 5' non-coding region to initiate viral 3D protein (RNA polymerase) for synthesis of viral RNA, and regulates the function of FMDV 3A protein to regulate the replication of the virus, and the like. Therefore, the present disclosure can relieve the ability of FMDV 3B protein to suppress host innate immune response by abolishing the immunosuppressive function of FMDV 3B protein without affecting other functions of FMDV 3B protein, thereby reducing the pathogenicity of FMDV to the host, while not affecting the production performance of FMDV in the FMDV propagation cell line BHK-21 which is defective in interferon production. The method of the present disclosure can be used to prepare a recombinant FMDV vaccine strain.

Preferably, a method for losing the immunosuppressive function of FMDV 3B protein may include a gene deletion technology, a gene mutation technology, and a gene insertion technology. The object of the present disclosure is to lose only the immunosuppressive function of FMDV 3B protein without affecting other functions of FMDV 3B protein. The changes of conformation, physical and chemical properties of FMDV 3B protein, or the changes of binding force of FMDV 3B protein to host protein may lead to the loss of immunosuppressive function of FMDV 3B protein. The commonly-used methods in the art include the gene deletion technology, the gene mutation technology, and the gene insertion technology and other genetic engineering technologies. According to the common knowledge of those skilled in the art, in addition to the above ones, the conformation, physical and chemical properties of FMDV 3B protein, or the binding force of FMDV 3B protein to host protein may also be changed using other gene editing methods, resulting in the loss of the immunosuppressive function of FMDV 3B protein.

Preferably, the method for losing the immunosuppressive function of FMDV 3B protein may be as follows: deleting or mutating amino acids at the position 17 of three copies 3B1, 3B2, and 3B3 of FMDV 3B protein.

Preferably, the method for losing the immunosuppressive function of FMDV 3B protein may be as follows: mutating amino acids at the position 17 of three copies 3B1, 3B2, and 3B3 of FMDV 3B protein.

Preferably, the method for losing the immunosuppressive function of FMDV 3B protein may be as follows: mutating the position 17 of an amino acid sequence of three copies 3B1, 3B2 and 3B3 of FMDV 3B protein into a polar amino acid.

Preferably, the method for losing the immunosuppressive function of FMDV 3B protein may be as follows: mutating the position 17 of an amino acid sequence of three copies 3B1, 3B2 and 3B3 of FMDV 3B protein into a glutamate using gene mutation technology. According to the common knowledge of those skilled in the art, in addition to the above ones, the position 17 of the amino acid sequence of three copies 3B1, 3B2 and 3B3 of FMDV 3B protein can be mutated using other gene editing methods, such that the conformation, physical and chemical properties of FMDV 3B protein, or the binding force of FMDV 3B protein to host protein are changed, resulting in the loss of the immunosuppressive function of FMDV 3B protein.

The present disclosure further provides a recombinant FMDV losing only the immunosuppressive function of a parental FMDV 3B protein. FMDV 3B protein not only has the immunosuppressive function, but also binds to the N-terminal of the 5' non-coding region to initiate viral 3D protein (RNA polymerase) for synthesis of viral RNA and regulate the function of FMDV 3A protein, thereby affecting the replication of the virus, and the like. Therefore, the present disclosure can relieve the ability of FMDV 3B protein to suppress the innate immune response by losing only the immunosuppressive function of FMDV 3B protein without affecting other functions of FMDV 3B protein, thereby reducing the pathogenicity of FMDV to the host and successfully constructing a recombinant FMDV.

Preferably, the parental FMDV 3B protein may have an amino acid sequence set forth in SEQ ID NO:4 or SEQ ID NO:7.

Preferably, the method for losing the immunosuppressive function of FMDV 3B protein may be as follows: deleting or mutating amino acids at the position 17 of three copies 3B1, 3B2, and 3B3 of the parental FMDV 3B protein.

Preferably, the method for losing the immunosuppressive function of FMDV 3B protein may be as follows: mutating the position 17 of an amino acid sequence of three copies 3B1, 3B2 and 3B3 of FMDV 3B protein into a polar amino acid.

Preferably, the method for losing the immunosuppressive function of FMDV 3B protein may be as follows: mutating the position 17 of an amino acid sequence of three copies 3B1, 3B2 and 3B3 of the parental FMDV 3B protein into a polar amino acid. According to the common knowledge of those skilled in the art, in addition to the above ones, the position 17 of the amino acid sequence of three copies 3B1, 3B2 and 3B3 of FMDV 3B protein may be mutated using other gene editing methods, such that the conformation, physical and chemical properties of FMDV 3B protein are changed, resulting in the loss of the immunosuppressive function of the 3B protein.

Preferably, the mutated 3B protein may have an amino acid sequence set forth in SEQ ID NO:2 or SEQ ID NO:6.

The present disclosure further provides a recombinant FMDV vaccine strain including the above recombinant FMDV.

The present disclosure further provides a preparation method of a recombinant FMDV, including the following steps:
(1) constructing a full-length infectious clone of an FMDV;
(2) mutating amino acids at the position 17 of three copies 3B1, 3B2, and 3B3 of a 3B protein to polar amino acids using gene mutation technology, e.g. polymerase chain reaction (PCR) site-directed mutagenesis, or gene synthesis technology including on the basis of the full-length infectious clone of an FMDV;
(3) transfecting FMDV-sensitive cells with a eukaryotic expression plasmid containing the polar amino acids mutated at the position 17 of the 3B1, 3B2, and 3B3 proteins, to obtain the recombinant FMDV.

Preferably, the FMDV-sensitive cell may be a BHK-21 cell or a porcine kidney (IBRS-2) cell.

Preferably, the mutation is that the position 17 of an amino acid sequence of the three copies 3B1, 3B2 and 3B3 of the 3B protein is mutated into to glutamate. According to the common knowledge of those skilled in the art, in addition to the above ones, the position 17 of the amino acid sequence of the three copies 3B1, 3B2 and 3B3 of FMDV 3B protein may be mutated using other gene editing methods, such that the conformation, physical and chemical properties of FMDV 3B protein, or the binding force of FMDV 3B protein to host protein are changed, resulting in the loss of the immunosuppressive function of the 3B protein and successfully constructing a recombinant FMDV.

Preferably, the mutated 3B protein may have an amino acid sequence set forth in SEQ ID NO:2 or SEQ ID NO:6.

The present disclosure further provides a recombinant FMDV prepared according to the above preparation method.

The present disclosure further provides a recombinant FMDV vaccine strain including the above recombinant FMDV.

The present disclosure further provides a recombinant FMDV vaccine prepared according to the above recombinant FMDV vaccine strain.

In addition, the present disclosure provides use of the recombinant FMDV vaccine in the preparation of a medicine for preventing and/or controlling FMD of an animal.

Preferably, the FMD may include a type-O FMD and a type-A FMD, and the animal may be selected from the group consisting of pig, cow and sheep.

The present disclosure has the following beneficial effects:
(1) The present disclosure confirms that FMDV 3B protein has an immunosuppressive function in different cell lines by using different methods such as type-I interferon and quantitative polymerase chain reaction (qPCR), and the 3B protein may be used to prepare immunosuppressants.
(2) On the basis of confirming that the 3B protein has an immunosuppressive function, a recombinant FMDV and a recombinant vaccine strain may be prepared by losing the immunosuppressive function of FMDV 3B protein.
(3) The present disclosure further selects the key sites for 3B protein to exert immunosuppressive function. The immunosuppressive function is relieved by introducing amino acid mutations at key sites in the three repeated copies of the 3B protein, and the mutations will not affect the replication of FMDV. Accordingly, a recombinant FMDV with a lost immunosuppressive function is successfully constructed and rescued.
(4) The recombinant FMDV is stably passaged in an FMDV propagation cell line BHK-21 that is defective in interferon production, but does not affect the virus yields, and has good production performance. Moreover, the recombinant FMDV has declined virulence in pig-derived host cells, and exerts a stronger inducing ability of innate immune response.
(5) In order to improve the antigen matching and antigen broad spectrum of the recombinant FMDV, the present disclosure provides a constructing method of a recombinant vaccine strain: using an established reverse genetic operating system containing a strain with a relatively-strong cellular immune response induction activity as a framework, screening an O/JSCZ/2013 strain that is cross-protective against different lineages of type-O FMDV as an antigen backbone, and mutating immunosuppressive sites of the 3B protein to construct a recombinant type-O FMDV vaccine strain; using an A/WH/CHA/09 strain, which has high antigen matching and strong cross-immunity protection, as an antigen backbone, and mutating the immunosuppressive sites of the 3B protein to construct a type-A recombinant FMDV vaccine strain. An inactivated vaccine is prepared using the above mentioned recombinant vaccine strain. The vaccine may promote an early immune response in animals and induce high levels of antibody production, thereby improving the biological safety and immune effectiveness. Therefore, the vaccine has good application prospects.

BRIEF DESCRIPTION OF THE DRAWINGS

FIG. 9 shows a result of expression analysis of IFN-β and interferon-induced antiviral genes in the recombinant FMDV with the 3B protein losing an immunosuppressive function, or its parental virus infected pig-derived cells, where r3B is a parental virus, r3B-A/E is a recombinant FMDV with 3B protein mutation.

DETAILED DESCRIPTION OF THE EMBODIMENTS

In order to make the technical means, creative features, objectives, and efficacies of the disclosure easy to understand, the disclosure will be further described below in combination with examples. The protection scope of the present disclosure is not limited thereto.

The relevant experiments described in the following examples have obtained a biosafety license and a FMD laboratory activity license.

According to the relevant requirements of biosafety level 3 (BSL-3) laboratory and FMD-related biosafety, the Lanzhou Veterinary Research Institute of the Chinese Academy of Agricultural Sciences has reported to the Biosafety Committee of the Lanzhou Veterinary Research Institute, the Biosafety Committee of the Chinese Academy of Agricultural Sciences, and the Laboratory Animal Ethics Committee of the Lanzhou Veterinary Research Institute. The Lanzhou Veterinary Research Institute of the Chinese Academy of Agricultural Sciences has obtained a permission of the Ministry of Agriculture to conduct research on highly-pathogenic FMDV pathogens and animals, and has put on record on the Ministry of Agriculture and Rural Affairs, thereby meeting the requirements of the national biosafety level.

The experimental cells and plasmid sources described in the examples are as follows:

FLAG-CMV-7.1 eukaryotic expression vector and POK12 vector are commercial plasmids; IFN-β, ISRE and NF-kB reporter systems are purchased from Miaoling Plasmid Sharing Platform; Trans5α Escherichia coli competent cells are purchased from TIANGEN Biotech (Beijing) Co., Ltd.; and HEK293T cells and BHK-21 cells are purchased from the National Infrastructure of Cell Line Resource.

Unless otherwise specified, the operations in the experiment are known in the art.

Example 1 Immunosuppressive Effect of FMDV 3B Protein

Figure 1:
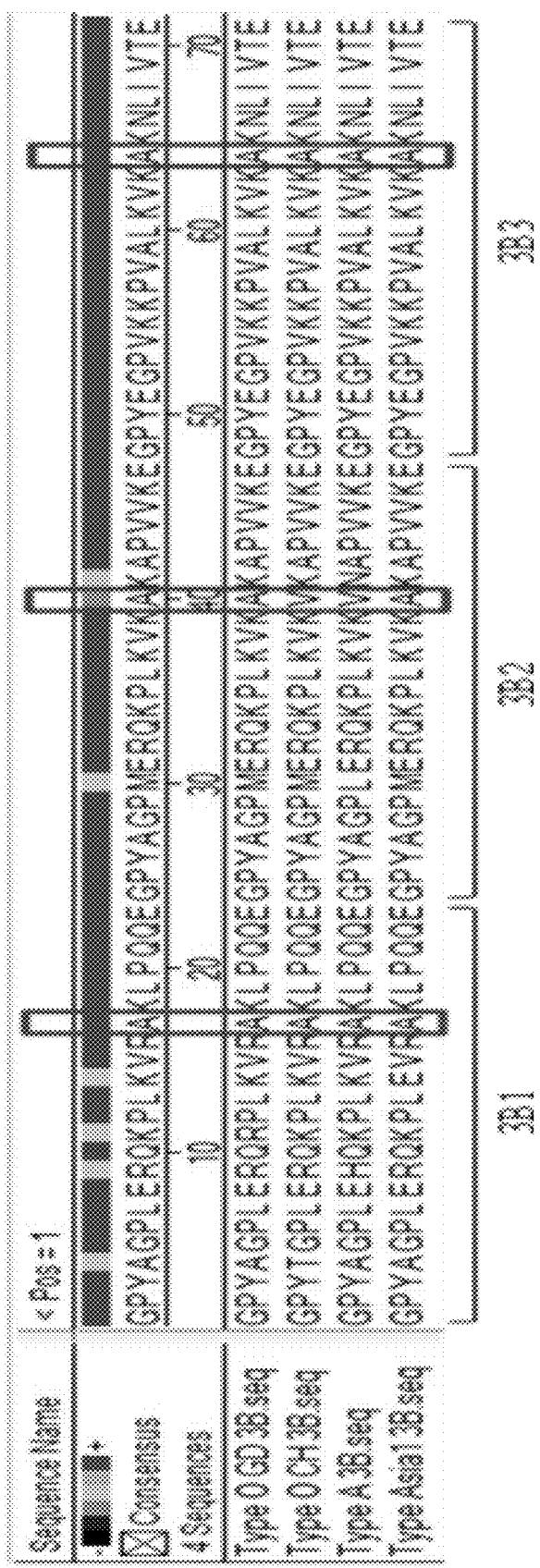
FIG. 1 shows an alignment analysis of amino acid sequence of FMDV 3B protein of different serotypes.

Amino acid sequences of 3B protein of different serotypes of FMDV were aligned, and it was found that three copies 3B1, 3B2, and 3B3 of 3B protein of different serotypes of FMDV, all had high homology. The results were shown in FIG. 1. Therefore, in this example, only an epidemic virus strain O/BY/CHA/2010 was taken as an example to study the immunosuppressive function of the 3B protein of the epidemic virus strain. The specific experiments were as follows:

1.1 Effect of FMDV 3B Protein on Innate Immune Response

The immunosuppressive effect of 3B protein was detected using IFN-β, ISRE and NF-kB reporter systems: HEK293T cells were transfected with FLAG-3B plasmid and IFN-β, ISRE or NF-kB reporter system plasmids for 24 h, stimulated by an interferon-induced model virus, e.g. Sendai virus (SeV), and the expression change of the reporter system was detected using a Luciferase kit (Promega).

A construction process of the FLAG-3B plasmid was as follows:

The O/BY/CHA/2010 strain used was preserved by the National Foot-and-Mouth Disease Reference Laboratory designated by the Veterinary Bureau of the Ministry of Agriculture, and the public might obtain the strain through the authorization letter approved by the Veterinary Bureau of the Ministry of Agriculture.

FMDV 3B gene sequence was deposited in the NCBI database, and primers were designed, a forward primer I was 3B-HindIII-F: CTCAAGCTTGCCACCATGGGACCC-TACGCCGGACCACT (SEQ ID NO:9, the underlined part was a HindIII restriction site); and a reverse primer II was 3B-BamHI-R: ATGGATCCTCACTCAGTGACGAT-CAAGTTCT (SEQ ID NO:10, the underlined part was a BamHI restriction site). Total RNA from PK-15 cells infected with O/BY/CHA/2010 strain was extracted, cDNA was synthesized by reverse transcription with random primers, the cDNA was used as a template, PCR amplification was conducted using the 3B-HindIII-F and 3B-BamHI-R, purified and collected 3B fragments were digested with HindIII and BamHI restriction enzymes (the nucleotide sequence was set forth in SEQ ID NO:3, and the amino acid sequence was set forth in SEQ ID NO:4). FLAG-CMV-7.1 vector was digested with the same restriction enzymes at 37° C. for 2 h, and nucleic acid electrophoresis was conducted to recover linearized fragments of the FLAG-CMV-7.1 vector containing sticky terminuses.

The purified and recovered linearized fragments of the FLAG-CMV-7.1 were ligated with the purified and recovered 3B fragments. A ligation product was placed overnight at 16° C., Trans5α Escherichia coli competent cells was transformed using the ligation product; after overnight culture, a single clone was picked and shaken in an ampicillin antibiotic-resistant LB liquid medium for 12 h, extracted using an Omega Plasmid Extraction Kit and the samples were sent for DNA sequencing to confirm the successful construction of the plasmid, and the obtained plasmid was named as FLAG-3B.

Experimental methods for transfection and interferon reporter system detection were as follows:

HEK293T cells were seeded in a 48-well culture plate; after the cells grew to 70% density, the reporter plasmid system was co-transfected with FLAG-CMV-7.1 vector or FLAG-3B plasmid for 24 h, an upper culture medium was aspirated, and the remaining culture was rinsed twice with PBS, and inoculated with the interferon-induced model virus SeV or the medium. 16 hours after SeV infection, the culture medium was discarded, the cell samples were rinsed with PBS twice, treated with Luciferase kit reagents, the fluorescence was measured with a Promega GloMax 20/20 luminescence detector, and the differential expression change in Luciferase of reporter system was analyzed. Remaining lysate was used for sodium dodecyl sulfate polyacrylamide gel electrophoresis (SDS-PAGE) experiment; the expression of 3B protein was detected using a FLAG antibody.

Figure 2:
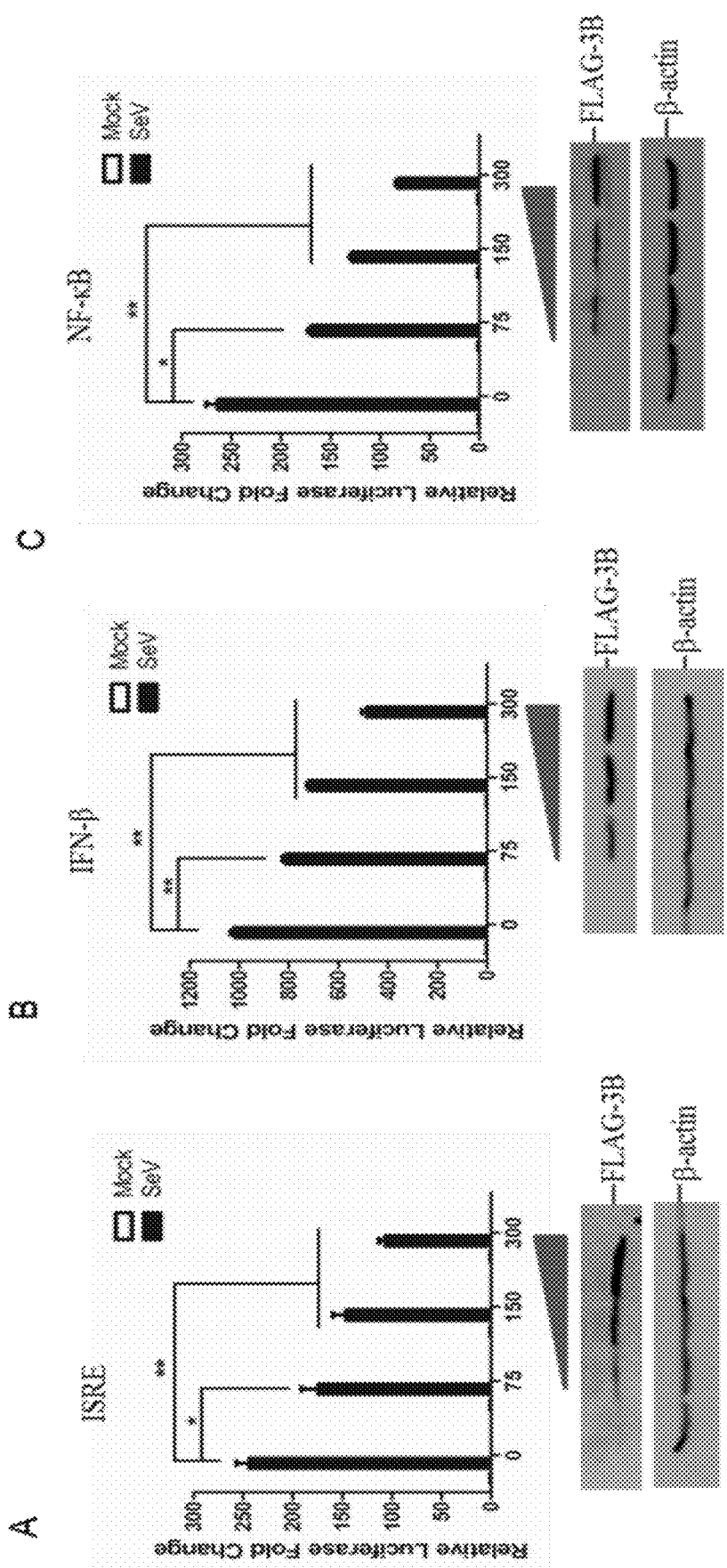
FIG. 2 shows an inhibitory effect of FMDV 3B protein on the activation of innate immune response pathways.

The results are shown in FIG. 2. After overexpression of 3B protein in HEK293T cells, the activation of ISRE, IFN-β, and NF-κB reporter systems induced by SeV stimulation all decreased significantly, and the increase of 3B protein expression led to more obvious suppression showing a dose-dependent manner. This indicates that FMDV 3B protein can suppress the activation of ISRE, IFN-β, and NF-κB pathways in the innate immune system, and has the function of suppressing the innate immune response.

1.2 Effect of a 3B Protein on SeV-Induced IFN-β mRNA Expression

Figure 3:
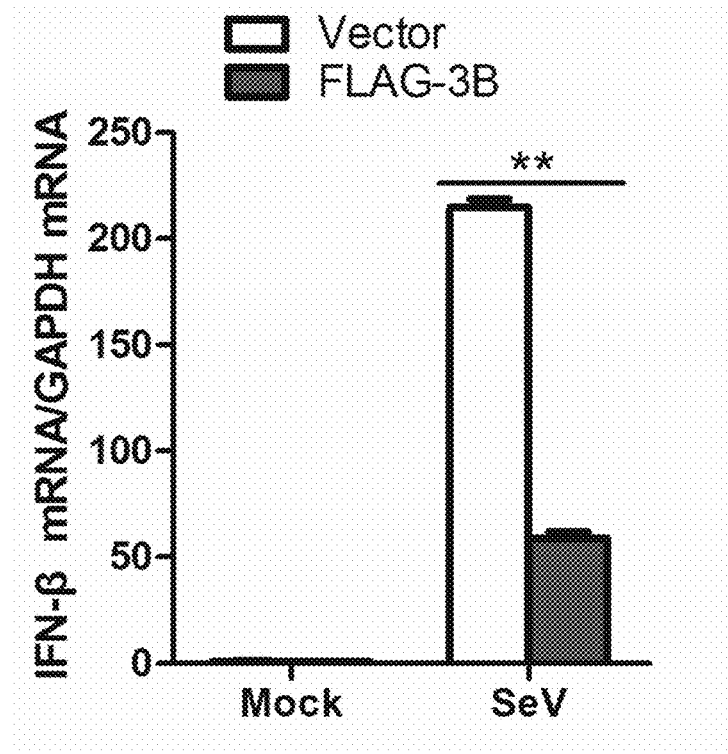
FIG. 3 shows a detection of the role of FMDV 3B protein on inhibiting the expression of type-I interferon.

The effect of 3B protein on SeV-induced IFN-β mRNA expression was further detected using a real-time quantitative PCR method: HEK293T cells were seeded in a 6-well culture plate; after growing to 70% density, the cells were transfected with FLAG-CMV-7.1 vector or FLAG-3B plasmid for 24 h, an upper culture medium was aspirated, and the remaining culture was rinsed twice with PBS, and inoculated with SeV or the medium. 16 hours after SeV infection, the culture medium was discarded; the cell samples were rinsed twice with PBS, and collected. Total RNA from cell samples was extracted with an RNA extraction kit, and cDNA was synthesized by reverse transcription with random primers. The level of IFN-β mRNA expression was detected by real-time quantitative PCR. The results are shown in FIG. 3. The SeV infection can induce a large amount of IFN-β expression. However, after overexpression of 3B protein in HEK293T cells, the IFN-β expression induced by SeV stimulation significantly decreased, indicating that 3B protein can significantly inhibit the expression of IFN-β mRNA.

Figure 4:
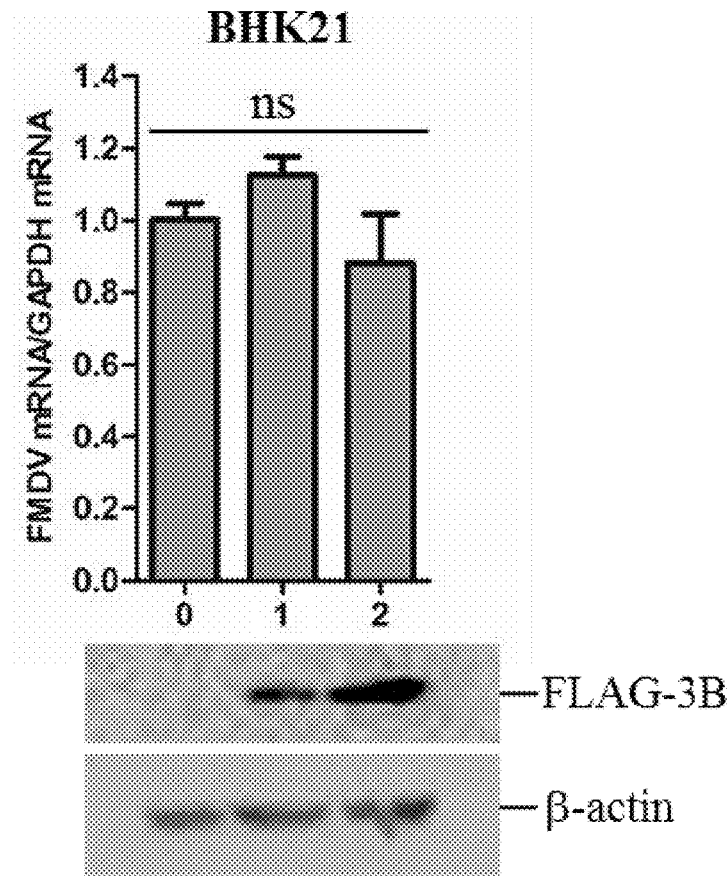
FIG. 4 shows a detection of the effect of 3B protein on FMDV replication in BHK-21 cells.

BHK-21 cells (a cell line with innate immune pathway immunodeficiency) were seeded in a 6-well plate, after growing to a monolayer, the cells were transfected with FLAG-CMV-7.1 vector or FLAG-3B plasmid for 24 h, FMDV was inoculated to infect the cells for 12 h, the culture medium was discarded, cell samples were rinsed twice with PBS, and collected. Total RNA from cell samples was extracted with an RNA extraction kit, and cDNA was synthesized by reverse transcription with random primers. FMDV RNA expression was detected by real-time quantitative PCR. The results are shown in FIG. 4. Since BHK-21 cells have no sound immune response pathway, overexpression of 3B protein in the innate immune pathway immunodeficiency BHK-21 cells did not affect the replication of FMDV. This indicates that the 3B protein does not regulate the replication of FMDV in the FMDV vaccine production engineering cell line BHK-21, and has potential application in the production process of the FMDV vaccine.

Figure 5:
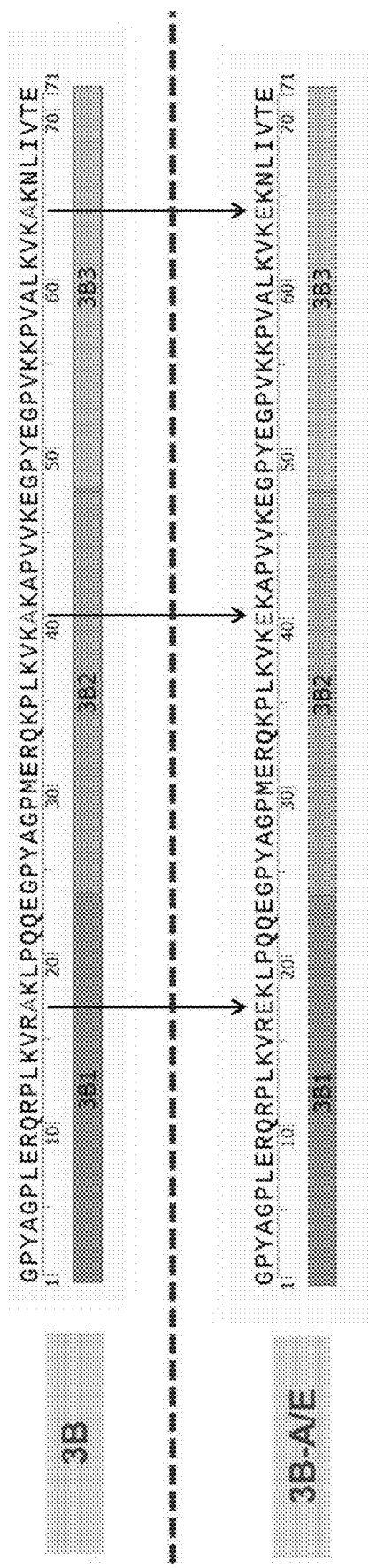
FIG. 5 shows a construction strategy of mutants with a lost immunosuppressive function of 3B protein.

Example 2 Constructing Method of a Eukaryotic Expression Plasmid of FMDV 3B Protein Mutant On the basis of Example 1, the 3B protein of an FMDV O/BY/CHA/2010 strain was mutated, and a eukaryotic expression plasmid of FMDV 3B protein mutant was constructed. The eukaryotic expression plasmids of other serotypes of FMDV 3B protein mutants could also be constructed using the method described in the example. The specific process was as follows:

A mutation strategy was shown in FIG. 5. On the basis of the 3B protein of a wild-type FMDV O/BY/CHA/2010 strain (the nucleotide sequence was set forth in SEQ ID NO:3, and the amino acid sequence was set forth in SEQ ID NO:4), the 3B protein gene coding sequence (the nucleotide sequence was set forth in SEQ ID NO:1, and the amino acid sequence was set forth in SEQ ID NO:2) in which an amino acid at the position 17 of 3B1, an amino acid at the position 17 of 3B2, and an amino acid at the position 17 of 3B3 were all mutated to glutamate was synthesized using gene synthesis technology; and an EcoRI restriction enzyme site was added at an N-terminus of the gene sequence and a BamHI restriction enzyme site was added at a C-terminus of the gene sequence. A FLAG-CMV-7.1 eukaryotic expression plasmid was digested with EcoRI and BamHI restriction enzymes to obtain a linearized vector fragment of about 4.7 kb. The synthesized fragment was ligated with the linearized FLAG-CMV-7.1 vector fragment, a ligation product was transformed into Trans5α *Escherichia coli* competent cells, and a recombinant plasmid was cloned and amplified. The constructed plasmid was sent to GENEWIZ Biotechnology Co., Ltd. for DNA sequencing analysis and confirmed that the 3 amino acid positions of FMDV 3B protein were successfully mutated. The resulting plasmid containing the 3 successfully-mutated amino acid sites was named as FLAG-3B-A/E.

Example 3 Effect of a 3B Protein Mutant on the Expression of a Type-I Interferon To further test the effect of 3B-A/E of 3B protein mutant with loss of the immunosuppressive sites on the expression of type-I interferon. HEK293T cells were seeded in a 6-well plate, after growing to 70% density, the cells were transfected with the same amount of FLAG-CMV-7.1 vector, FLAG-3B plasmid or FLAG-3B-A/E plasmid for 24 h; an upper culture medium was aspirated, the remaining culture was rinsed twice with PBS, and inoculated with an interferon-induced model virus SeV to infect for 16 h; the culture medium was discarded, the cell samples were rinsed twice with PBS, and collected at 16 h postinfection. Total RNA from cell samples was extracted with an RNA extraction kit, and cDNA was synthesized by reverse transcription with random primers. IFN-β mRNA expression change was evaluated using real-time quantitative PCR, samples were parallelly prepared, total cell protein was extracted, sodium dodecyl sulphate-polyacrylamide gel electrophoresis (SDS-PAGE) was conducted, and expression of mutant 3B protein was detected by Western blotting.

Figure 6:
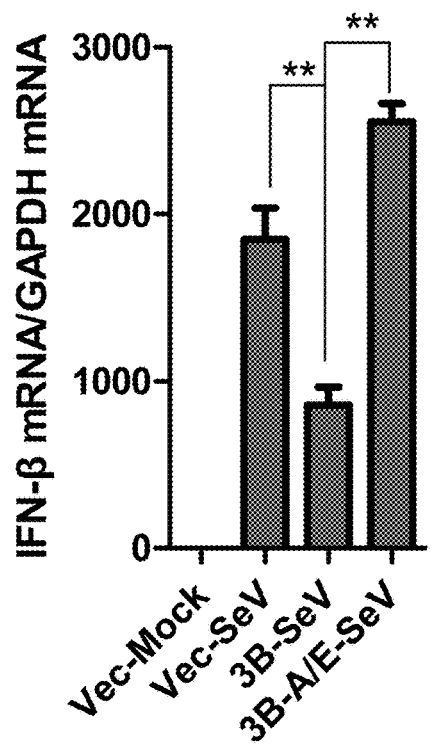
FIG. 6 shows a detection of inhibitory ability of a mutant with a lost immunosuppressive function of 3B protein to interferon 13 (IFN-β) expression, where 3B-A/E is a mutant of 3B protein.

The experimental results are shown in FIG. 6. The results indicate that under the same expression level, the wild-type 3B protein can suppress the expression of IFN-β mRNA while the 3B-A/E of 3B protein mutant with loss of the immunosuppressive sites cannot suppress the IFN-β mRNA expression. The above results indicate that after mutation of the amino acid at the position 17 of 3B1, the amino acid at the position 17 of 3B2 and the amino acid at the position 17 of 3B3 to glutamate, the 3B protein loses the ability to suppress host innate immune response. Therefore, mutations based on the above sites can guide the construction of recombinant viruses and recombinant vaccine strains with elimination of the immunosuppression activity of 3B protein to improve the effectiveness of FMDV vaccine.

In summary, although the above examples only mutate the amino acid at the position 17 of the three copies 3B1, 3B2, and 3B3 of the 3B protein of FMDV O/BY/CHA/2010 strain to glutamate, the 3B protein loses the ability to suppress host innate immune response. However, the three copies 3B1, 3B2 and 3B3 of FMDV 3B protein have high homology among different serotypes of FMDV, with a sequence alignment shown in FIG. 1. Therefore, according to the common knowledge of those skilled in the art, the amino acids at the position 17 of the three copies 3B1, 3B2 and 3B3 of the 3B proteins of different serotypes of FMDV can also be mutated to glutamate, such that the 3B proteins of different serotypes of FMDV lose the ability to suppress host innate immune response. This can also guide the construction of recombinant FMDVs and recombinant FMDV vaccine strains with elimination of 3B protein-mediated immunosuppression to improve vaccine effectiveness.

In addition, the objective of the example is to remove the immunosuppressive function of FMDV 3B protein. The changes of the conformation, physical and chemical properties of FMDV 3B protein or the binding force of FMDV 3B protein to the host protein can cause the loss of the immunosuppressive function of FMDV 3B protein as well. The genetic engineering methods commonly-used in this field such as gene deletion technology, gene mutation technology, and gene insertion technology, etc., can change the conformation, physical and chemical properties of FMDV 3B protein or the binding force of FMDV 3B protein to the host protein, resulting in the loss of the immunosuppressive function of FMDV 3B protein. According to the common knowledge of those skilled in the art, in addition to the above ones, the loss of the immunosuppressive function of FMDV 3B protein may also be changed using other gene editing methods.

Example 4 Construction of a Recombinant FMDV with 3B Protein Mutation

4.1 Construction of an Infectious Clone of a Recombinant FMDV

According to an FMDV genome sequence published in GenBank, an amplification primer that introduces rescue elements and the entire genome of FMDV was designed and synthesized, and appropriate restriction sites were introduced. Total viral RNA was extracted using RNAeasy Mini Kit (Qiagen), the first-strand cDNA was synthesized by reverse transcription using a primer oligNot I (5'-ttttctagagcggccgct$_{38}$-3', set forth in SEQ ID NO:11), a 20 µL reaction system was prepared using a PrimeScript Reverse Transcriptase with extremely strong extension ability (from TaKaRa Bio) according to the product specification, and reacted at 42° C. for 1 h for later use; and gene fragments covering the entire virus genome were obtained by PCR amplification using a segmented amplification primer, and the reverse-transcribed first-strand cDNA was used as the template. The amplification adopted an LA Taq® polymerase (from TaKaRa Bio) that is suitable for long fragment amplification and has excellent performance, and a 50 µL reaction system was prepared according to a product specification; the amplification was conducted at 94° C. for 5 min, 94° C. for 30 s, 57° C. for 30 s, 72° C. for 3 min (with an extension of 1 kb/min), 35 cycles; then 72° C. for 10 min; a PCR amplification product was purified and recovered, and ligated to obtain a full-length genome sequence of FMDV; where a 5'-terminus upstream of the viral genome included sequences of a human cytomegalovirus RNA polymerase II promoter, a murine RNA polymerase I promoter and a ribozyme, and a 3'-terminus downstream of the nucleic acid sequence of the virus included sequences of a ribozyme, a murine polymerase terminator I and a polymerase terminator II.

On the basis of obtaining FMDV eukaryotic expression plasmids, the 3B gene in the FMDV genome was subjected to point mutations using PCR site-directed mutagenesis and other gene mutation techniques or gene synthesis techniques. Accordingly, a recombinant eukaryotic plasmid with the amino acids at the position 17 of three copies 3B1, 3B2, 3B3 of the 3B protein all mutated to glutamate was obtained.

4.2 Rescue of a Recombinant Virus

BHK-21 cells, when growing to 80% density, were used for transfection; 4 µg of recombinant eukaryotic plasmid was transfected into BHK-21 cells under the mediation of a Lipofectamine™ 2000 (Invitrogen); meanwhile, a liposome control and a normal cell control were set up, which were placed in a 37° C. incubator containing 5% $CO_2$. The cell status was recorded to observe the cytopathic alterations; the recombinant virus was harvested when about 90% of the cells become round and refractile, and inoculated with BHK-21 cells again after repeated freezing and thawing for 3 times until the virus could stably produce cytopathic effect (CPE); the cells became rounded, aggregated into a botryoid distribution and finally disintegrated into fragments, and a recombinant virus with FMDV 3B protein losing an immunosuppressive function was obtained.

In this example, only amino acids at the position 17 of three copies 3B1, 3B2, and 3B3 of the 3B protein of the FMDV strain were mutated to glutamate, such that the 3B protein lost the ability to suppress the innate immune response. Since the three copies 3B1, 3B2 and 3B3 of FMDV 3B protein had high homology among different serotypes of FMDV, with a sequence alignment shown in FIG. 1. Therefore, according to the common knowledge of those skilled in the art, the amino acids at the position 17 of the three copies 3B1, 3B2 and 3B3 of the 3B proteins of different serotypes of FMDV can also be mutated to glutamate, such that the 3B proteins of different serotypes of FMDV lost the ability to suppress host innate immune response. This can also guide the construction of recombinant viruses with elimination of 3B protein-mediated immunosuppression to obtain recombinant FMDVs with loss of the immunosuppressive function of 3B protein.

In addition, the objective of the example is to lose the immunosuppressive function of FMDV 3B protein. The conformation, physical and chemical properties of FMDV 3B protein or the binding force of FMDV 3B protein to the host protein could cause the loss of the immunosuppressive function of FMDV 3B protein. The genetic engineering methods commonly-used in this field such as gene deletion technology, gene mutation technology, and gene insertion technology, etc., change the conformation, physical and chemical properties of FMDV 3B protein or the binding force of FMDV 3B protein to the host protein, resulting in the loss of the immunosuppressive function of FMDV 3B protein. According to the common knowledge of those skilled in the art, in addition to the above ones, the loss of the immunosuppressive function of FMDV 3B protein may also be changed using other gene editing methods.

Example 5 Construction and Identification of a Recombinant Type-O FMDV Vaccine Strain with 3B Protein Mutation

5.1 Construction of an Infectious Clone of a Recombinant Type-O FMDV

The O/JSCZ/2013 virus strain used was preserved by the National Foot-and-Mouth Disease Reference Laboratory designated by the Veterinary Bureau of the Ministry of Agriculture, and the public might obtain the strain through the authorization letter approved by the Veterinary Bureau of the Ministry of Agriculture.

A pair of amplification primers, OP12A-F (5'-TTTTCCT-TAAGGGACAGGAACACGCCGTGTTTGCCTGCGT-3', set forth in SEQ ID NO:12) and OP12A-R (5'-ACTCA-CATCGATGTCAAAGTGAAACCTTC-3', set forth in SEQ ID NO:13), were designed and synthesized according to the genome sequence of the O/JSCZ/2013 virus strain; the total viral RNA of O/JSCZ/2013 virus strain was extracted using RNAeasy Mini Kit (Qiagen), the first-strand cDNA was synthesized by reverse transcription using a primer oligNotI (5'-ttttctagagcggccgct$_{38}$-3'), a 20 µL reaction system was prepared using a PrimeScript Reverse Transcriptase with extremely strong extension ability (from TaKaRa Bio) according to a product specification, and reacted at 42° C. for 1 h for later use; and the primers OP12A-F and OP12A-R were mixed with cDNA nucleic acid of the O/JSCZ/2013 virus strain using a reverse-transcribed first-strand cDNA as the template, and the amplification was conducted to obtain gene fragments of the O/JSCZ/2013 virus strain. The amplification adopted an LA Taq® polymerase (from TaKaRa Bio) that is suitable for long fragment amplification and has excellent performance, and a 50 µL reaction system was prepared according to a product specification; the amplification was conducted at 94° C. for 5 min, 94° C. for 30 s, 57° C. for 30 s, 72° C. for 3 min and 30 s, 35 cycles; then 72° C. for 10 min; a PCR amplification product was purified and recovered, with a size of 3591 bp, and the nucleotide sequence was set forth in SEQ ID NO:5.

The obtained gene fragments containing a L gene, a P1 gene and a P2 gene of the O/JSCZ/2013 virus strain and an eukaryotic expression plasmid prO/CHA/99 of a rescue system of the O/CHA/99 strain of type-O FMDV were subjected to double digestion using AflII and ClaI, separately; corresponding target fragments were purified and recovered, and ligated and transformed into JM109 competent cells, and positive clones were identified by DNA sequencing to obtain a recombinant plasmid prO-FMDV containing the L gene, the P1 gene and the P2 gene of the O/JSCZ/2013 virus strain (disclosed in the authorized patent "Recombinant bivalent inactivated vaccine for foot-and-mouth disease (FMD) and preparation method and use thereof", ZL201710256450.0, the full text of which was incorporated into this application by reference).

The N-terminus of PolyA of the FMDV genome sequence 3'UTR in the recombinant plasmid prO-FMDV was a restriction endonuclease cleavage site SbfI; the recombinant plasmid prO-FMDV was subjected to double digestion with ClaI and SbfI and ligated into the POK12 vector to obtain a plasmid POK-3B containing the 3B gene fragment; point mutation was conducted on the 3B gene using the plasmid as a template and using mutation primers as follows: m3B1-F(5'-AAAACCTCTGAAAGTGAGAgagAAGCTCC-CACAGCAG-3', set forth in SEQ ID NO:14); m3B1-R(5'-CTGCTGTGGGAGCTTctcTCTCACTTTCAGAGGTTTT-3', set forth in SEQ ID NO:15); m3B2-F(5'-GAAACCGCTGAAAGTGAAAgagAAAGCCCCGGTC GTT-3', set forth in SEQ ID NO:16); m3B2-R(5'-AACGACCGGGGCTTTctcTTT-CACTTTCAGCGGTTTC-3', set forth in SEQ ID NO:17); m3B3-F(5'-TGTCGCTTTGAAAGT-GAAAgagAAGAACTTGATTGTC-3', set forth in SEQ ID NO:18); m3B3-R(5'-GACAATCAAGTTCTTctcTTT-CACTTTCAAAGCGACA-3', set forth in SEQ ID NO:19). The process specifically included: mutation for 3B1 was conducted using the POK-3B as the template, with m3B1-F and m3B1-R mutation primers, to obtain a 3B1 mutant plasmid; mutation for 3B2 was conducted using the 3B1 mutant plasmid as the template, with m3B2-F and m3B2-R mutation primers, to obtain a 3B2 mutant plasmid; and mutation for 3B3 was conducted using the 3B2 mutant plasmid as the template, with m3B3-F and m3B3-R mutation primers, to obtain a recombinant plasmid in which the amino acids of position 17 of the 3B1, 3B2, and 3B3 were all mutated to glutamate. The amplification adopted a high-fidelity PrimeSTAR® HS DNA polymerase (from TaKaRa Bio), and a 50 µL reaction system was prepared according to a product specification; the amplification was conducted at 95° C. for 5 min, 95° C. for 1 min, 55° C. for 1 min, 68° C. for 6 min, 20 cycles; then 68° C. for 10 min. The PCR amplification product was digested with DpnI to digest and remove the template plasmid, and then transformed into DH5a competent cells, and the positive clones were identified by DNA sequencing. A mutated 3B plasmid POK-m3B was obtained, where an amino acid encoded by the mutated 3B gene was set forth in SEQ ID NO:6.

The obtained recombinant plasmid POK-m3B containing the 3B with the amino acids of position 17 of the 3B1, 3B2, and 3B3 all mutated to glutamate was subjected to double digestion with ClaI and SbfI to prepare target fragments; the target fragments were ligated with vector fragments recovered from the recombinant type-O eukaryotic plasmid prO-FMDV that was subjected to double digestion with ClaI and SbfI, the recombinant plasmids were then transformed into DH5a competent cells, and the positive samples were sent for DNA sequencing analysis to confirm the successful mutations in 3 amino acid sites of 3B gene, and obtain a recombinant plasmid prO-m3B-FMDV containing the 3B gene mutation.

5.2 Rescue of a Recombinant Virus

Figure 7:
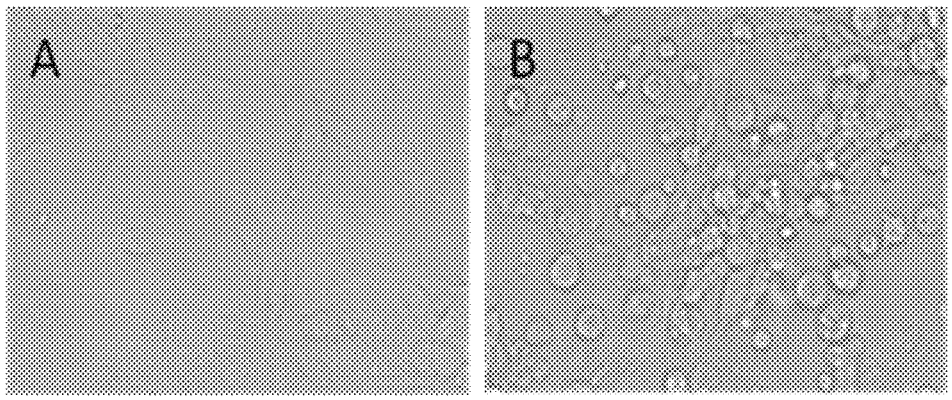
FIG. 7 shows a rescue result of a recombinant type-O FMDV with 3B protein losing an immunosuppressive function.

BHK-21 cells, when growing to 80% density, were used for transfection; 4 µg of recombinant plasmid prO-m3B-FMDV was transfected into BHK-21 cells under the mediation of a Lipofectamine™ 2000 (Invitrogen); meanwhile, a liposome control and a normal cell control were set up, which were placed in a 37° C. incubator containing 5% $CO_2$ to observe the CPE; the virus was harvested when about 90% of the cells had CPE, and inoculated onto BHK-21 cells again after repeated freezing and thawing for 3 times until the virus could stably produce CPE; the cells became rounded, aggregated into a botryoid distribution and finally disintegrated into fragments. The results are shown in FIG. 7, where A is a picture of normal control BHK-21 cells, and B is a picture of CPE in BHK-21 cells infected with the rescued recombinant virus rO-m3B-FMDV. The rescued recombinant virus rO-m3B-FMDV could stably produce CPE after infecting BHK-21 cells, and the cells became rounded, aggregated into a botryoid distribution and disintegrated, and a recombinant type-O FMDV was successfully obtained and named as rO-m3B-FMDV.

5.3 Identification of Recombinant Virus by RT-PCR

The supernatant of BHK-21 cells that were infected with the stably-passaged recombinant virus rO-m3B-FMDV was collected, and the total RNA was extracted with RNAeasy Mini Kit (Qiagen); after reverse transcription, the 3B-containing gene fragments were amplified, purified and recovered, and sent for DNA sequencing. The results show that the 3B gene of the obtained recombinant type-O FMDV vaccine strain is consistent with the theoretical sequence, and the amino acids at the position of 17 in the three copies 3B1, 3B2, and 3B3 are all glutamate.

In summary, in order to improve the antigen matching and antigen broad spectrum of the recombinant FMDV, the example provides a constructing method of a recombinant type-O vaccine strain: using an established reverse genetic operating system of a virus strain with a relatively strong cellular immune response induction activity as the framework (a eukaryotic expression plasmid prO/CHA/99 of the type-O FMDV O/CHA/99 strain rescue system), and replacing with the screening-obtained O/JSCZ/2013 antigen genes that are cross-protective to different lineages of type-O FMDV; meanwhile, this provides a method of mutating the immunosuppressive sites of 3B protein to construct a recombinant type-O FMDV vaccine strain with reduced immunosuppression activity. Although in this example, only the amino acids at the position 17 of the three copies 3B1, 3B2, and 3B3 of the virus framework (type-O FMDV O/CHA/99) 3B protein are mutated to glutamate, such that the 3B protein loses the ability to suppress host innate immune response, and the recombinant type-O FMDV vaccine strain with reduced immunosuppression activity is constructed. Since the three copies 3B1, 3B2 and 3B3 of FMDV 3B protein have high homology among different serotypes of FMDV, with a sequence alignment shown in FIG. 1, according to the common knowledge of those skilled in the art, the amino acids at the position 17 of the three copies 3B1, 3B2 and 3B3 of the 3B proteins of different serotypes of FMDV as a framework can also be mutated to glutamate, such that the 3B proteins of different serotypes of FMDV lose the immunosuppressive function. This can also successfully construct the recombinant FMDV vaccine strain of different serotypes with reduced immunosuppression activity.

In addition, the objective of the example is to lose the immunosuppressive function of FMDV 3B protein. The changes of the conformation, physical and chemical properties of FMDV 3B protein or the binding force of FMDV 3B protein to the host protein can cause the loss of the immunosuppressive function of FMDV 3B protein. The genetic engineering methods commonly-used in this field such as gene deletion technology, gene mutation technology, and gene insertion technology, etc., can change the conformation, physical and chemical properties of FMDV 3B protein or the binding force of FMDV 3B protein to the host protein, resulting in the loss of the immunosuppressive function of FMDV 3B protein. According to the common knowledge of those skilled in the art, in addition to the above ones, the loss of the immunosuppressive function of FMDV 3B protein may also be changed using other gene editing methods.

Example 6 Construction and Identification of a Recombinant Type-A FMDV Vaccine Strain with 3B Protein Mutation 6.1 Construction of an Infectious Clone of a Recombinant Type-A FMDV The A/WH/CHA/09 virus strain used was preserved by the National Foot-and-Mouth Disease Reference Laboratory designated by the Veterinary Bureau of the Ministry of Agriculture, and the public might obtain the strain through the authorization letter approved by the Veterinary Bureau of the Ministry of Agriculture.

A pair of amplification primers, AP1-F(5'-TTTTCCT-TAAGGGACAGGAACATGCTGTGTTTGCCTGCGT-3', set forth in SEQ ID NO:20) and AP1-R(5'-TATTTT-CACCGGTGCAATAATTTTCTGCTTGTGTCTGTC-3', set forth in SEQ ID NO:21), were designed and synthesized according to a genome sequence of the A/WH/CHA/09 virus strain; the total viral RNA of A/WH/CHA/09 virus strain was extracted using RNAeasy Mini Kit (Qiagen), the first-strand cDNA was synthesized by reverse transcription using a primer oligNot I (5'-ttttctagagcggccgct$_{38}$-3'), a 20 µL reaction system was prepared using a PrimeScript Reverse Transcriptase with extremely strong extension ability (from TaKaRa Bio) according to a product specification, and reacted at 42° C. for 1 h for later use; and amplification was conducted using primers AP1-F and AP1-R. A reverse-transcribed first-strand Cdna was used as the template to obtain gene fragments of the A/WH/CHA/09 virus strain. The amplification adopted an LA Taq® polymerase (from TaKaRa Bio) that is suitable for long fragment amplification which has excellent performance, and a 50 µL reaction system was prepared according to a product specification; the amplification was conducted at 94° C. for 5 min, 94° C. for 30 s, 57° C. for 30 s, 72° C. for 2 min and 30 s, 35 cycles; then 72° C. for 10 min; a PCR amplification product was purified and collected, with the nucleotide sequence set forth in SEQ ID NO:8.

Gene fragments containing a part of the L gene and P1 gene of the obtained A/WH/CHA/09 virus strain and the plasmid prO/CHA/99 of the rescue system of the O/CHA/99 virus strain of the type-O FMDV were subjected to double digestion using AflII and SgrAI, separately; corresponding target fragments were purified and collected, and ligated and transformed into JM109 competent cells, and the positive clones were identified by DNA sequencing to obtain a recombinant plasmid prA-FMDV containing a part of the L gene and P1 gene of the A/WH/CHA/09 virus strain (disclosed in the authorized patents "Recombinant bivalent inactivated vaccine for foot-and-mouth disease (FMD) and preparation method and use thereof", ZL201710256450.0, and "Recombinant type-A foot-and-mouth disease (FMD) vaccine strain and preparation method and use thereof", ZL201310175324.4, the full text of which were incorporated into this application by reference).

The N-terminus of PolyA of the FMDV genome sequence 3'UTR in the recombinant plasmid prA-FMDV was a restriction endonuclease cleavage site SbfI; the recombinant plasmid prA-FMDV was subjected to double digestion with SgrAI and SbfI and ligated into the POK12 vector to obtain a plasmid POK-s3B containing the 3B gene fragments; point mutation was conducted on the 3B gene using the plasmid as the template and using the mutation primers and the method described in 5.1 of Example 5; and the plasmid POK-ms3B of the mutated 3B was obtained, and the amino acids encoded by the mutated 3B was set forth in SEQ ID NO:6.

The obtained recombinant plasmid POK-ms3B containing the amino acids of position 17 of the 3B1, 3B2, and 3B3 all mutated to glutamate was subjected to double digestion with SgrAI and SbfI to prepare target fragments; the target fragments were ligated with vector fragments recovered from the recombinant type-A eukaryotic plasmid prA-FMDV that was subjected to double digestion with SgrAI and SbfI, and then transformed into DH5α competent cells. The DNA sequencing was carried out to identify positive clones, and confirmed successful mutations in 3 amino acid sites of 3B gene, to obtain a recombinant plasmid prA-m3B-FMDV containing the 3B gene mutation.

6.2 Rescue of a Recombinant Virus

Figure 8:
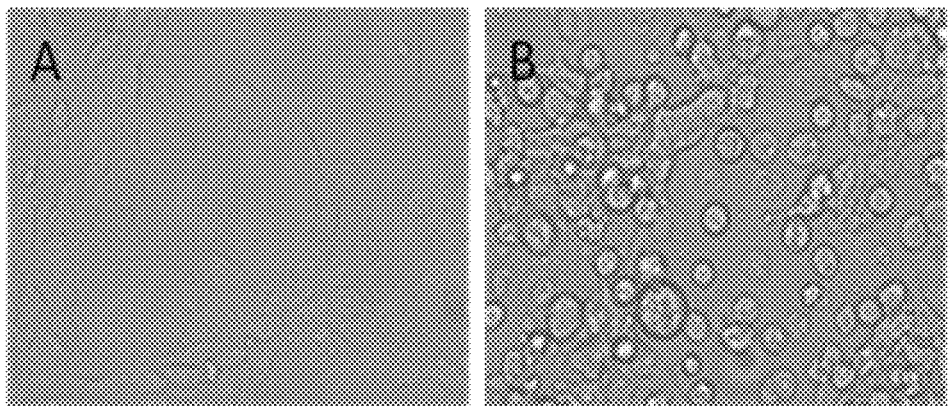
FIG. 8 shows a rescue result of a recombinant type-A FMDV with 3B protein losing an immunosuppressive function.

BHK-21 cells, when growing to 80% density, were used for transfection; 4 µg of recombinant plasmid prA-m3B-FMDV was transfected into BHK-21 cells under the mediation of a Lipofectamine™ 2000 (Invitrogen); meanwhile, a liposome control and a normal cell control were set up, which were placed in a 37° C. incubator containing 5% $CO_2$ to observe the CPE; the virus was harvested when about 90% of the cells had CPE, and inoculated to BHK-21 cells again after repeated freezing and thawing for 3 times until the virus could stably produce CPE; the cells became rounded, aggregated into a botryoid distribution and finally disintegrated into fragments. The results are shown in FIG. 8, where A is a picture of normal control BHK-21 cells, and C is a picture of CPE in BHK-21 cells infected with a rescued recombinant virus rA-m3B-FMDV. The rescued recombinant virus rA-m3B-FMDV could stably produce CPE after infecting BHK-21 cells, the cells became rounded, aggregated into a botryoid distribution and disintegrated, and the recombinant type-A FMDV was successfully obtained and named as rA-m3B-FMDV.

6.3 RT-PCR Identification of Recombinant Virus

The supernatant of BHK-21 cells that were infected with the stably-passaged recombinant virus rA-m3B-FMDV was collected, and the total RNA was extracted with RNAeasy Mini Kit (Qiagen). After reverse transcription, the 3B-containing gene fragments were amplified, purified and recovered, and sent for DNA sequencing. The results show that the 3B gene of the obtained recombinant type-A FMDV is consistent with the theoretical sequence, and the amino acids at the position of 17 in the three copies 3B1, 3B2, and 3B3 are all glutamate.

In summary, in order to improve the antigen matching and antigen broad spectrum of the recombinant FMDV, the example provides a constructing method of a recombinant type-A vaccine strain: using an established reverse genetic operating system of a virus strain with a relatively strong cellular immune response induction activity as a framework (a eukaryotic expression plasmid prO/CHA/99 of the type-O FMDV O/CHA/99 strain rescue system), and replacing with the screening-obtained A/WH/09 antigen genes that have high antigen matching and strong cross-immunity protection; meanwhile, this provides a method of mutating the immunosuppressive site of 3B protein to construct a recombinant type-A FMDV vaccine strain with reduced immunosuppression activity. Although in this example, only the amino acids at the position 17 of the three copies 3B1, 3B2, and 3B3 of the virus framework (type-O FMDV O/CHA/99) 3B protein are mutated to glutamate, such that the 3B protein loses the ability to suppress host innate immune response, and the recombinant type-A FMDV vaccine strain with reduced immunosuppression activity is constructed. Since the three copies 3B1, 3B2 and 3B3 of FMDV 3B protein have high homology among different serotypes of FMDV, with a sequence alignment shown in FIG. 1, according to the common knowledge of those skilled in the art, the amino acids at the position 17 of the three copies 3B1, 3B2 and 3B3 of the 3B proteins of different serotypes of FMDV as a framework can also be mutated to glutamate, such that the 3B proteins of different serotypes of FMDV lose the immunosuppressive function. This can also successfully construct the recombinant FMDV vaccine strains of different serotypes with reduced immunosuppression activity.

In addition, the objective of the example is to lose the immunosuppressive function of FMDV 3B protein. The changes of conformation, physical and chemical properties of FMDV 3B protein or the binding force of FMDV 3B protein to the host protein can cause the loss of the immunosuppressive function of FMDV 3B protein. The genetic engineering methods commonly-used in this field such as gene deletion technology, gene mutation technology, and gene insertion technology, etc., can change the conformation, physical and chemical properties of FMDV 3B protein or the binding force of FMDV 3B protein to the host protein, resulting in the loss of the immunosuppressive function of FMDV 3B protein. According to the common knowledge of those skilled in the art, in addition to the above ones, the loss of the immunosuppressive function of FMDV 3B protein may also be changed using other gene editing methods.

Example 7 Detection and Analysis of Immunosuppressive Ability of a Recombinant FMDV with Mutations in 3B Protein Pig-derived PK-15 cells were infected with same amount of recombinant FMDV vaccine strain with 3B protein mutation, rO-m3B-FMDV, and its parental virus for 12 h, respectively. Cells were collected to extract RNA, and mRNA expression changes of IFN-β and interferon-induced antiviral genes ISG15, ISG56 and MX1 were detected by qPCR.

Figure 9:
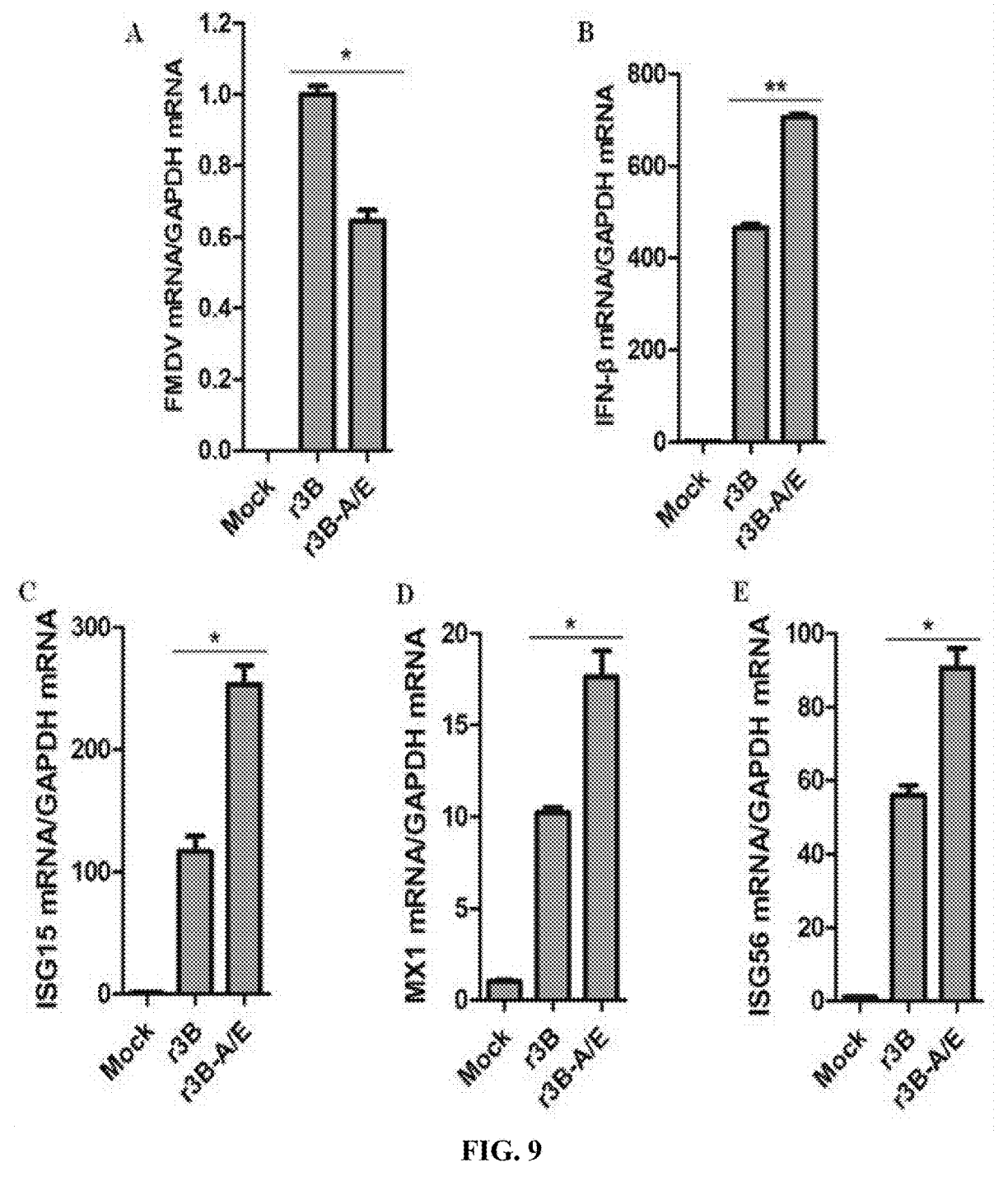

The experiment results are shown in FIG. 9, where A is a detection result of the FMDV by qPCR, B is a detection result of IFN-β content, C is a detection result of ISG15 content, D is a detection result of MX1 content, and E is a detection result of ISG56 content. The results indicate that the recombinant FMDV with mutations in 3B protein has significantly lower replication ability than its parental virus, but has an ability to induce stronger expression of IFN-β and interferon-induced antiviral genes ISG15, ISG56 and MX1 than its parental virus. The results also indicate that the recombinant FMDV with mutations in 3B protein has a significantly-reduced pathogenicity to host cells, and a greatly-increased ability to induce host innate immune responses. Therefore, the recombinant FMDV with mutations in 3B protein can be used as an FMDV vaccine seed to improve the biological safety of the vaccine and increase the vaccine immune efficacy.

Example 8 Pathogenicity Test of a Recombinant FMDV with 3B Protein Mutation on BHK-21 Cells BHK-21 cells were cultured according to a conventional method using the MEM culture medium containing 10% fetal bovine serum. The cells were seeded in a 12-well plate, and cultivated in an incubator containing 5% $CO_2$ at 37° C. until the cell monolayer reached about 90% confluence. Virus solution was diluted with MEM at a tenfold multiple proportion, the virus solutions of each dilution ($10^{-4.0}$ to $10^{-9.0}$) were added to the cell plate, with each dilution in 4 wells, placed in an incubator containing 5% $CO_2$ at 37° C. for cultivation and observed for 3 days, and the media tissue culture infective dose ($TCID_{50}$) to BHK-21 cells was determined by Reed-Muench's calculation method. The titer of rO-m3B-FMDV and rA-m3B-FMDV and the corresponding parental viruses rO-FMDV and rA-FMDV was determined according to the Reed-Muench's calculation method; the $TCID_{50}$ of rO-m3B-FMDV was calculated to be $10^{-8.33}$/mL, and the $TCID_{50}$ of control parental virus rO-FMDV was calculated to be $10^{-8.23}$/mL; meanwhile, the $TCID_{50}$ of rA-m3B-FMDV was calculated to be $10^{-8.33}$/mL, and the $TCID_{50}$ of control parental virus rA-FMDV was calculated to be $10^{-8.5}$/mL. The results indicate that the replication ability of the recombinant FMDV with 3B protein mutation in an FMDV engineering production cell line has no difference with its parent virus. In combination with the Example 7, the recombinant FMDV with mutations in 3B protein has a significantly-reduced pathogenicity to host cells, and a greatly-increased ability to induce host innate immune responses. Therefore, the recombinant FMDV with mutations in 3B protein can be used as a vaccine seed for FMDV, and has good production performance and higher biological safety.

Reed-Muench's calculation method is the existing technology in the art. The existing literature "Reed, L. J. and Muench, H. (1938). 'A Simple Method of Estimating Fifty Percent Endpoints'. The American Journal of Hygiene 27:493-497" has been described the method in detail; this literature is incorporated into this application for reference.

Example 9 Immune Evaluation of an Inactivated Vaccine Prepared by a Recombinant FMDV with 3B Protein Mutation 9.1 Preparation of FMDV Antigen The recombinant rO-m3B-FMDV and an epidemic virus strain O/BY/CHA/2010 were prepared using suspended BHK-21 cells (a preparation method of the suspended cells and parameters used were disclosed in the authorized patent "Recombinant bivalent inactivated vaccine for foot-and-mouth disease (FMD) and preparation method and use thereof", ZL201710256450.0, the full text of which was incorporated into this application by reference), the harvested virus liquid was the virus culture, and stored at −40° C. The virus cultures of the rO-m3B-FMDV and the O/BY/CHA/2010 were separately inactivated with a 3 mmol/L binary ethylenimine (BEI) (from Sigma-Aldrich) at 30° C. for 30 h; a blocking agent sodium thiosulfate solution was added, maintained overnight at 4° C., and stored for later use. After passing the security check, the inactivated antigen was tested for antigen content, and mixed with an ISA206 adjuvant (from SEPPIC, France) at a ratio of 1:1 to prepare the vaccine. The vaccine was specifically prepared in accordance with the procedures for inactivated vaccines against FMDV in veterinary biological products in the Chinese Pharmacopoeia.

9.2 Comparison Test of Vaccine Immune Effectiveness of Recombinant Vaccine Strain and Epidemic Virus Strain The experimental pigs were purchased from an FMD non-epidemic area, and tested by an FMDV liquid-phase blocking ELISA (LPB-ELISA) produced by the National Foot-and-Mouth Disease Reference Laboratory to detect Type-O antibodies, and the antibody titers are all less than 1:4. The 3ABC-ELISA antibody test result of FMD non-structural proteins detection was negative as well.

7 pigs were immunized with a vaccine of recombinant Type-O FMDV with 3B protein mutation (rO-m3B-FMDV) and 7 pigs were immunized with a vaccine prepared from epidemic virus strain (O/BY/CHA/2010) in the same dose of antigen separately; and on the 7 d, 14 d, 21 d, and 28 d after immunization, the antibody levels in serum were detected by type-O FMDV liquid-phase blocking ELISA (LPB-ELISA). 28 days later, a challenge experiment was conducted using the epidemic virus strain (O/BY/CHA/2010) with 1000 times of the $SID_{50}$ dose, 3 non-vaccinated pigs were set up as control, and the observation was recorded for 15 days.

The results are shown in Table 1. Recombinant type-O FMDV vaccine with 3B protein mutation can induce an early immune response and a prolongation of the duration of immunity leading to the rising of the antibody titer after immunization. The antibody response induced by the recombinant virus vaccine is earlier than that induced by the vaccine of epidemic virus strain, and the level of antibodies produced is also higher in the recombinant virus antigen vaccinated pigs than that vaccinated with the epidemic virus strain antigen. The virus challenge results show that the protection rate of the recombinant vaccine strain is 100%, which is higher than the protection rate (85.7%) of the vaccine prepared by the epidemic virus strain. The above results indicate that in comparison with the vaccine prepared by the epidemic virus strain, the vaccine prepared by the recombinant type-O FMDV vaccine with 3B protein mutation described in the present disclosure can achieve better immune response in animals.

TABLE 1

Comparison of antibody response and protection rate of recombinant type-O FMDV vaccine with 3B protein mutation and the vaccine prepared by epidemic virus strains in pigs.

| Group | SN | Immunizing dose | 7 d | 14 d | 21 d | 28 d | Protection status |
|---|---|---|---|---|---|---|---|
| rO-m3B-FMDV vaccine | 0487 | 2 mL | 1:22 | 1:64 | 1:128 | 1:360 | 7/7 |
| | 0476 | 2 mL | 1:45 | 1:90 | 1:256 | 1:256 | |
| | 0492 | 2 mL | 1:45 | 1:90 | 1:128 | 1:360 | |
| | 0495 | 2 mL | 1:180 | 1:256 | 1:360 | 1:720 | |
| | 0491 | 2 mL | 1:45 | 1:256 | 1:512 | 1:512 | |
| | 0478 | 2 mL | 1:64 | 1:90 | 1:128 | 1:180 | |
| | 0477 | 2 mL | 1:90 | 1:256 | 1:360 | 1:512 | |
| O/BY/CHA/2010 vaccine | 0488 | 2 mL | 1:16 | 1:90 | 1:90 | 1:128 | 6/7 |
| | 0497 | 2 mL | 1:22 | 1:45 | 1:128 | 1:180 | |
| | 0499 | 2 mL | 1:22 | 1:45 | 1:90 | 1:360 | |
| | 0489 | 2 mL | 1:11 | 1:22 | 1:45 | 1:90 | |
| | 0493 | 2 mL | <1:8 | 1:16 | 1:45 | 1:45 | |
| | 0475 | 2 mL | 1:22 | 1:64 | 1:128 | 1:360 | |
| | 0479 | 2 mL | 1:22 | 1:45 | 1:90 | 1:256 | |
| Control | 0490 | 0 | <1:8 | <1:8 | <1:8 | <1:8 | 0/3 |
| | 0496 | 0 | <1:8 | <1:8 | <1:8 | <1:8 | |
| | 0494 | 0 | <1:8 | <1:8 | <1:8 | <1:8 | |

The foregoing descriptions are only preferred implementations of the present disclosure. It should be noted that several improvements and modifications may further be made by a person of ordinary skill in the art without departing from the principle of the present disclosure, and such improvements and modifications should also be deemed as falling within the protection scope of the present disclosure.

What is claimed is:

1. A method for preparing a recombinant foot-and-mouth disease virus (FMDV), comprising mutating the amino acid at position 17 for each of 3B1, 3B2, and 3B3 of an FMDV 3B protein to glutamate to eliminate the immunosuppressive function of the FMDV 3B protein.

2. A recombinant FMDV, wherein the amino acid at position 17 for each of 3B1, 3B2, and 3B3 of an FMDV 3B protein is mutated to a polar amino acids using a gene mutation technology, thus eliminating the immunosuppressive function of the parental FMDV 3B protein.

3. A recombinant FMDV vaccine strain comprising the recombinant FMDV according to claim 2.

4. A method for preparing a recombinant FMDV, comprising the following steps:
   (1) constructing a full-length infectious clone of an FMDV;
   (2) mutating the amino acids at position 17 for each of 3B1, 3B2, and 3B3 of a 3B protein to a polar amino acids using a gene mutation technology or a gene synthesis technology to obtain a recombinant plasmid;
   (3) transfecting FMDV-sensitive cells with the recombinant plasmid, and culturing the transfected FMDV-sensitive cells to obtain the recombinant FMDV.

5. A recombinant FMDV prepared by the preparation method according to claim 4.

6. A recombinant FMDV vaccine strain comprising the recombinant FMDV according to claim 5.

7. An FMDV vaccine prepared from the recombinant FMDV vaccine strain according to claim 6.

8. The recombinant FMDV according to claim 2, wherein the amino acid sequence of the parental FMDV 3B protein is set forth in SEQ ID NO:4 and SEQ ID NO:7.

9. The recombinant FMDV according to claim 2, wherein the amino acids at position 17 for each of 3B1, 3B2, and 3B3 of the FMDV 3B protein is mutated to glutamate.

10. The recombinant FMDV according to claim 9, wherein the amino acid sequence of the mutated FMDV 3B protein is set forth in SEQ ID NO:2 and SEQ ID NO:6.

11. The method according to claim 4, wherein the FMDV-sensitive cell is the BHK-21 cell or porcine kidney (IBRS-2) cell.

12. The method according to claim 4, wherein the amino acids at position 17 for each of 3B1, 3B2 and 3B3 of the FMDV 3B protein are mutated to glutamate.

13. The method according to claim 12, wherein the mutated FMDV 3B protein has the amino acid sequence set forth in SEQ ID NO:2 or SEQ ID NO:6.

* * * * *